(12) United States Patent
Song et al.

(10) Patent No.: US 8,178,525 B2
(45) Date of Patent: May 15, 2012

(54) FXA INHIBITORS WITH CYCLIC AMIDOXIME OR CYCLIC AMIDRAZONE AS P4 SUBUNIT, PROCESSES FOR THEIR PREPARATIONS, AND PHARMACEUTICAL COMPOSITIONS AND DERIVATIVES THEREOF

(75) Inventors: Ho Young Song, Daejeon (KR); Young Lag Cho, Daejeon (KR); Dae Yon Lee, Daejeon (KR); Hee Sock Park, Daejeon (KR); Sung Yoon Baek, Daejeon (KR); Sang Eun Chae, Daejeon (KR); Sang Hui Jo, Daejeon (KR); Yeon Ok Kim, Daejeon (KR); Hyang Sook Lee, Daejeon (KR); Ju Hyun Park, Daejeon (KR); Tae Kyo Park, Daejeon (KR); Sung Ho Woo, Daejeon (KR); Yong Zu Kim, Daejeon (KR)

(73) Assignee: Legochem Bioscience Ltd., Daejeon (KR)

( * ) Notice: Subject to any disclaimer, the term of this patent is extended or adjusted under 35 U.S.C. 154(b) by 0 days.

(21) Appl. No.: 13/002,271

(22) PCT Filed: Jun. 5, 2009

(86) PCT No.: PCT/KR2009/003008
§ 371 (c)(1),
(2), (4) Date: Dec. 30, 2010

(87) PCT Pub. No.: WO2010/002115
PCT Pub. Date: Jan. 7, 2010

(65) Prior Publication Data
US 2011/0112083 A1    May 12, 2011

(30) Foreign Application Priority Data

Jul. 3, 2008 (KR) .................. 10-2008-0064178

(51) Int. Cl.
*C07D 413/12* (2006.01)
*C07D 413/14* (2006.01)
*C07D 487/04* (2006.01)
*A61K 31/5395* (2006.01)
*A61K 31/53* (2006.01)

(52) U.S. Cl. ............. 514/229.2; 514/241; 514/242; 544/66; 544/180; 544/182

(58) Field of Classification Search .......... 544/66, 544/180, 182; 514/229.2, 241, 242
See application file for complete search history.

(56) References Cited

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Banker, G.S. et al, "Modern Pharmaceutics, 3ed." Marcel Dekker, New York, 1996, pp. 451 and 596.*

* cited by examiner

*Primary Examiner* — Kahsay T Habte
(74) *Attorney, Agent, or Firm* — Sughrue Mion, PLLC

(57) ABSTRACT

Disclosed are novel oxazolidinone derivatives with cyclic amidoxime or cyclic amidrazone group, pharmaceutically acceptable salts thereof, methods for preparing the same and pharmaceutical compositions containing the same. The oxazolidinone derivatives with cyclic amidoxime or cyclic amidrazone group or the pharmaceutically acceptable salts thereof can be effectively used for the treatment of thromboembolism and tumor as an anticoagulant based on the inhibition of factor Xa.

7 Claims, 1 Drawing Sheet

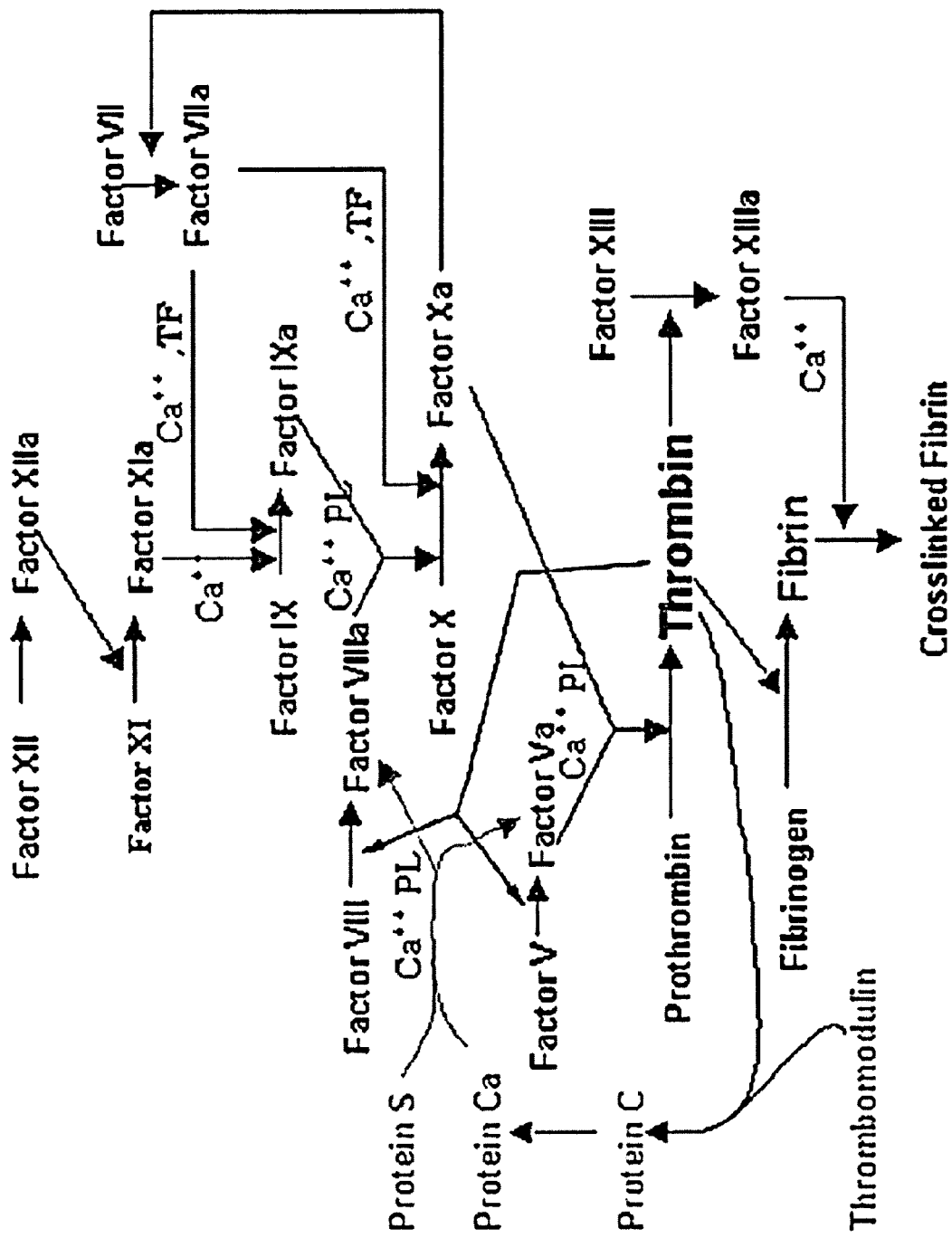

FXA INHIBITORS WITH CYCLIC AMIDOXIME OR CYCLIC AMIDRAZONE AS P4 SUBUNIT, PROCESSES FOR THEIR PREPARATIONS, AND PHARMACEUTICAL COMPOSITIONS AND DERIVATIVES THEREOF

CROSS REFERENCE TO RELATED APPLICATIONS

This application is a National Stage of International Application No. PCT/KR2009/003008 filed Jun. 5, 2009, which claims priority from Korean Patent Application No. 10-2008-0064178 filed Jul. 3, 2008, the contents of all of which are incorporated herein by reference in their entirety.

TECHNICAL FIELD

The present invention relates to a novel oxazolidinone derivatives with cyclic amidoxime or cyclic amidrazone group represented by formula I, pharmaceutically acceptable salts thereof, preparing methods thereof and pharmaceutical compositions containing the same.

[Formula I]

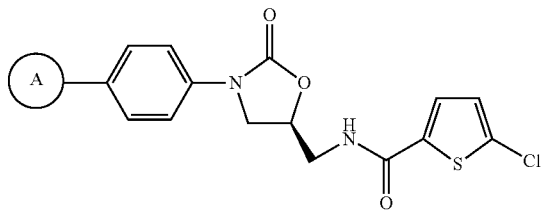

wherein,
ring A is a residue selected from the group consisting of following structures;

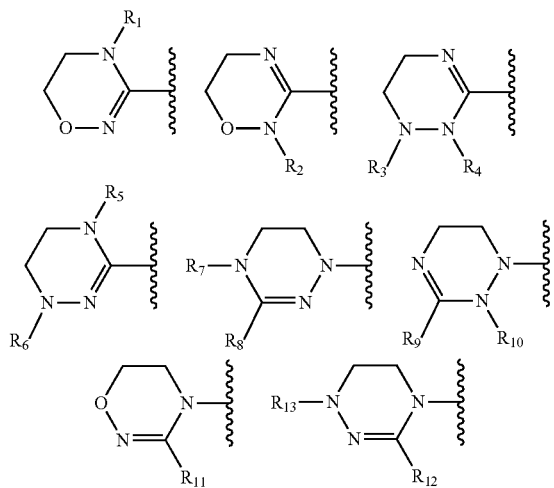

The antithrombotic and anticoagulant effect of the novel oxazolidinone derivatives with cyclic amidoxime or cyclic amidrazone group of the present invention represented by formula I is attributed to the inhibition of active clotting protease known as factor Xa or other active serine proteases such as factor VIIa, factor IXa or thrombin.

BACKGROUND ART

The blood coagulation factors are distributed in plasma, with various types of factors from $1^{st}$ coagulation factor to $13^{th}$ coagulation factor working in cascades fashion to result in blood coagulation. The mechanism wherein individual blood coagulation factors participate in blood coagulation is shown in FIG. 1.

As shown in FIG. 1, blood coagulation is accomplished by a series of reactions which are very sophisticated and complicated. In general, inactivated precursors are activated by specific active blood coagulation factors (indicated by "a" attached to the end of coagulation factor). Then, next blood coagulation factors are activated. Most of those activated blood coagulation factors are enzymes of serine protease family. They adhere on the surface of activated platelet at wound site and activate blood coagulation factors stepwise and finally produce fibrin clot, leading to hemostasis.

Thrombin is a multi-functional coagulation factor that is involved in the final stages of the coagulation cascades. Prothrombin, the precursor of thrombin, is activated by prothrombinase complex composed of factor Va, factor Xa, Ca++, and phospholipids (PL) to yield thrombin, which converts fibrinogen to fibrin. The generated fibrins cover the aggregated platelet to induce blood coagulation. Finally, fibrins are cross-linked by factor XIIIa to produce stable fibrin clot.

To produce prothrombinase complex, factor X has to be activated to factor Xa, which is mainly mediated by Xase complex. Factor VIIIa, factor IXa, Ca++ and phospholipids (PL) generated via intrinsic pathway or factor VIIa, tissue factor (TF) and Ca++ generated via extrinsic pathway work as Xase complex.

Thrombin also activates factor V and factor VIII. When thrombin is over-produced, blood vessel itself may be clogged. To avoid the clogging, thrombin triggers blood coagulation inhibition action. That is, thrombin is binding to thrombomodulin to activate protein C. The activated protein C (APC), complexed with protein S, inactivates the factor Va and factor VIIIa.

In fact, factor Xa itself is a serine protease, and involved in the complicated blood coagulation process. Factor Xa, as an essential member of prothrombinase complex, is acting as a catalyst for conversion of prothrombin to thrombin. Thrombin converts fibrinogen into fibrin monomers and the fibrin monomers thus generated is involved in the generation and the stabilization of thrombus. Thus, over or inappropriate production of thrombin might result in thromboembolism. Therefore, the inhibition of thrombin itself or thrombin generation may result in the reduction of fibrin production involved in thrombus formation, leading to the prevention of thromboembolism.

In brief, the inhibition of factor Xa results in the inhibition of thrombin production, by which thromboembolism can be prevented or alleviated. The compound represented by formula I in the present invention and the pharmaceutically acceptable salt thereof can inhibit factor Xa, which eventually, according to the above logic, leads to the prevention of thromboembolic diseases (MI, stroke, PE, etc.).

Among compounds known as factor Xa inhibitors, antistasin (ATS) and tick anti-coagulant peptide (TAP) are representative protein inhibitors. ATS (composed of 119 amino acids) is a natural peptide isolated from leech, having Ki value of 0.05 nM against factor Xa. TAP is also a peptide isolated from tick which is composed of 60 amino acids and has Ki value of 0.5 nM against factor Xa. However, these inhibitors are in limited clinical use; only heparin or its sulfated polysaccharide analogues are in clinical use with some limitation.

A low molecular compound was developed as a blood coagulation inhibitor, particularly factor Xa inhibitor which is described in WO9529189. In the meantime, WO9933800 describes factor Xa inhibitor having indole moieties. In addition, diverse factor Xa inhibitors are discovered and in the process of development. For example, heterocyclic compound having nitrogen atom (WO2004058743), imidazole derivatives (WO2004050636), pyrazole derivatives (WO2004056815), indole-2-carboxamide derivatives (WO2003044014), oxybenzamide derivatives (WO2002051831), guanidine/amidine derivatives (WO2002046159), amino-bicyclic pyrazinone/pyridinone derivatives (WO2004002405), etc.

To be clinically useful, as FXa inhibitors, these molecules should have high antithrombotic effect, high stability in both plasma and liver, proper selectivity to other related serine proteases (thrombin, trypsin, cathepsin G, etc), low toxicity, and satisfactory bioavailability.

The most advanced compound having oxazolidinone, similar to that of the present invention, is Rivaroxaban (formula A), which is now at phase III clinical evaluation. Some oxazolidinone derivatives represented by formula 2 are described in WO 01/47917. However, some of these compounds are reported to have limited solubility; a specific example of the problem is Rivaroxaban. The solubility of Rivaroxaban is only 8 mg/L. The poor solubility may give rise to a lot of practical limitations including variability, and slow dissolution. These problems may be circumvented by introducing a highly soluble moiety.

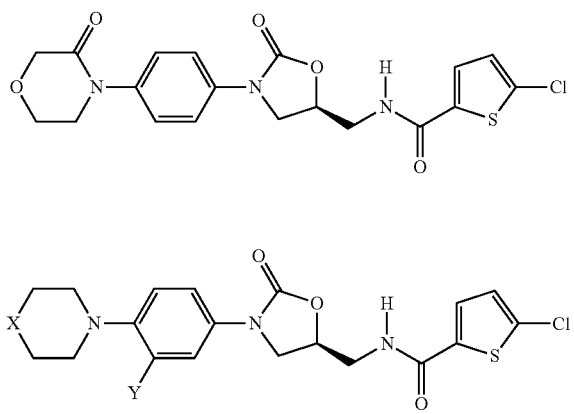

[Formula A]

X = CH$_2$, O, S, N—R
Y = — NCOR'

WO 2004/83174 describes the use of pyrazole derivatives including Apixaban. Some of these inhibitors are cyclic amidine and sulfonyl amidine derivatives represented by formula C.

However, there is no precedent similar to the present invention which describes the specific introduction of cyclic amidoxime or cyclic amidrazone in oxazolidinone scaffold as factor Xa inhibitors. In fact, little is known about the substantiation of cyclic amidoxime or cyclic amidrazone in drug design.

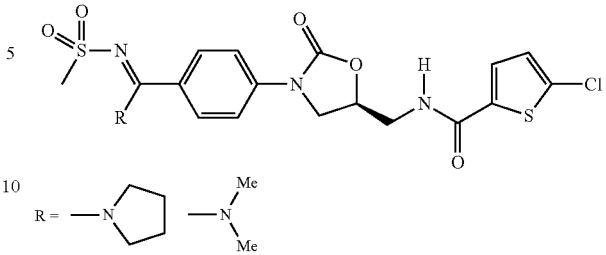

[Formula C]

The major trend of recent studies on FXa and thrombin inhibitor is the implementation of amidine functions. The amidine function, so called P1 group, is designed to bind Asp$^{189}$ located on the bottom of S1 pocket. Both FXa and thrombin recognize arginine residue in natural substrate as the P1 site. Amidine group (including guanidine derivatives) replacing guanidine in arginine is highly hydrophilic. Thus, inhibitors with amidine function are generally not well absorbed, and even if they are absorbed, they are cleared too fast due to the intrinsic high polarity of the amidine (Drugs of the Future, 1999, 24(7), 771).

Amidine itself has a strongly basic character (PKa: approximately 12.5). Due to a formal positive charge at physiological condition, the amidine inhibitor generally shows poor absorption. Therefore, it needs to be changed to less basic alternatives. Representative examples of these are pyridine derivative, amidrazone, cyclic amine, alkylamine derivative, aminobenzisoxazole, etc (U.S. Pat. No. 6,958,356). There are also fundamentally different approaches to circumvent these problems, including amidoximes. Amidoxime is easily synthesized by adding hydroxyl group to amidine structure, which is a prodrug based on that weak N—O bond is easily reduced to amidine in vivo. This approach takes advantage of that PKa of amidoxime is remarkably lower (8-9) than that of amidine. Ximelagatran is another example of the same type of prodrug. This trend is seen not only in the study of FXa inhibitor but also in the study of thrombin inhibitor. However, most of these attempts turned out to be not as good as expected. As a third class of attempt, neutral P1 groups are introduced. Unlike other class of drugs, FXa and thrombin inhibitors tend to show good efficacy when they are at high concentrations in blood. Moreover, the concentration of free drug, unbound to serum proteins in blood, is very important. In the case of neutral P1 group inhibitor, protein binding tends to be high, resulting in poorer efficacy than expected.

To overcome these problems, the present inventors introduced relatively polar group at other positions than P1 site, with a neutral group fixed at P1 site. Parallel to the logic, some other important factors to improve pharmaceutical effect are included, which are as follows: 1) Substantial improvement of water-solubility; 2) Low plasma protein binding; when free concentration of the drug is high, the efficacy in PT assay increased likewise even though FXa binding affinity is somewhat compromised.

The site selected for the introduction of polar group in this invention is P4 sub-site of inhibitor, and the logic behind the selection is as follows. S4 site of FXa has U-shaped binding site, surrounded by three faces with Tyr99, Phe174, and Trp215. The binding site is composed of only aromatic amino acid side chains, which is different from thrombin surrounded by Leu99, Ile174, and Trp215. The difference is exploited in the drug design.

S4 pocket of FXa is good at interaction with cationic residue, which is generally called "π-cation interaction". In fact, some inhibitors are designed and synthesized to have positive charge in P4 sites. In this invention, cyclic amidoxime or amidrazone is introduced in P4 site, in order to improve water-solubility and increase drug effect by reducing protein binding, as mentioned above. The reason of selection cyclic form is that the inventors believed that absorption could be improved by reducing number of NH bonds which generally shows negative effect on absorption. According to recent studies, it is more advantageous for a drug to have less hydrogen bond donor (HBD) than hydrogen bond acceptor (HBA). According to Lipinski's Rule, up to 10 HBAs are possibly accepted but HBD is limited only up to 5 (Adv. Drug Delivery Rev., 2001, 46, 3-26) and particularly in the case of new drug the number of average HBDs is approximately 2, suggesting that HBD is more strictly restricted (J. Med. Chem. 2004, 47, 6338-48). Amidoxime or amidrazone group itself has basic character, which enables easier separation-purification-storage as a salt form, and as a result, water-solubility is expected to be increased.

In short, we introduced amidoxime or amidrazone at P4 site. To reduce number of HBD, we used cyclic form of the function to make more drug-like inhibitors.

The compounds of formula I of the present invention were in fact confirmed to have the aforementioned advantages. Water-solubility and protein binding level are presented, together with 2×PT value and Ki.

DISCLOSURE OF INVENTION

Technical Problem

The present inventors synthesized novel oxazolidinone derivatives with cyclic amidoxime or cyclic amidrazone group having useful properties, which can be applied to preparations of pharmaceutical formulations. Particularly, the oxazolidinone derivatives with cyclic amidoxime or cyclic amidrazone group demonstrate FXa inhibiting effect, so that they can be used for treating or preventing of thrombosis, myocardial infarction, arteriosclerosis, inflammatory, apoplexy, angina pectoris, recurrent stricture after angioplasty, and thromboembolism such as intermittent claudication. Further, the oxazolidinone derivatives with the cyclic amidoxime or cyclic amidrazone according to the present invention can serve as the inhibitor against factor VIIa, factor IXa, and thrombin which are coagulant factors in blood coagulation cascade.

It is an object of the present invention to provide novel oxazolidinone derivatives with cyclic amidoxime or cyclic amidrazone group exhibiting factor Xa-inhibiting property or pharmaceutically acceptable salts thereof.

It is another object of the present invention to provide a pharmaceutical composition for anticoagulation comprising oxazolidinone derivatives with cyclic amidoxime or cyclic amidrazone group or the pharmaceutically acceptable salts thereof as an active ingredient.

It is also an object of the present invention to provide a pharmaceutical composition comprising oxazolidinone derivatives with cyclic amidoxime or cyclic amidrazone group or the pharmaceutically acceptable salts thereof as an active ingredient for treating or preventing of thrombosis, myocardial infarction, arteriosclerosis, inflammation, stroke, angina pectoris, restenosis, intermittent claudication, phlebothrombosis, pulmonary embolism, arterial thrombosis, myocardial ischemia or thromboembolism.

It is further an object of the present invention to provide a pharmaceutical composition for treating or preventing treatment of coronary artery disease, cerebral artery disease and peripheral artery disease, characteristically co-treated with oxazolidinone derivatives with cyclic amidoxime or cyclic amidrazone group or the pharmaceutically acceptable salts thereof and a thrombolytic agent.

It is also an object of the present invention to provide a use of oxazolidinone derivatives with cyclic amidoxime or cyclic amidrazone group or the pharmaceutically acceptable salts thereof as an anticoagulant for preserving blood, plasma or blood products in vitro.

Technical Solution

The present invention relates to a novel oxazolidinone derivatives with cyclic amidoxime or cyclic amidrazone group represented by formula I or the pharmaceutically acceptable salts thereof, preparing methods of the same and pharmaceutical compositions comprising the same.

[Formula I]

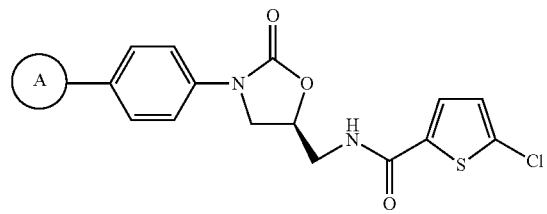

wherein, ring A is a residue selected from the group consisting of following structures;

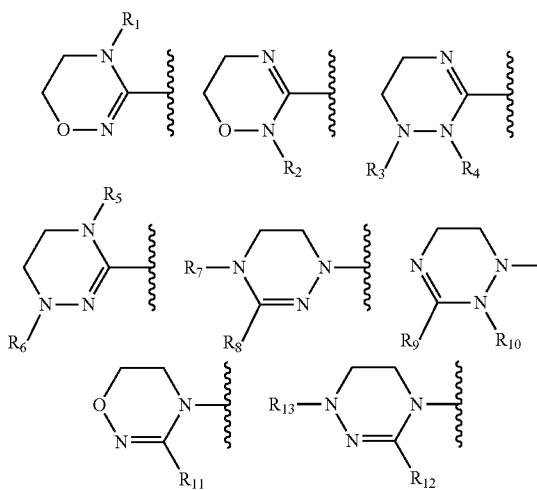

$R_1$ through $R_{12}$ are independently H, $(C_1-C_7)$alkyl, $(C_3-C_7)$cycloalkyl, $(C_6-C_{12})$aryl or $(C_4-C_{12})$heteroaryl containing one to four heteroatom(s) selected from the group consisting of O, S and N, $R_3$ and $R_4$ form a ring by connecting with $(C_3-C_5)$alkylene, carbon atom of the alkylene can be substituted with carbonyl, and the alkyl, cycloalkyl, aryl or heteroaryl of the $R_1$ through $R_{12}$ may be substituted with any one selected from the group consisting of $(C_1-C_7)$alkyl, halo$(C_1-C_7)$alkyl, $(C_1-C_7)$alkoxy and halogen;

$R_{13}$ is H, $(C_1-C_7)$alkyl, $(C_3-C_7)$cycloalkyl, formyl, $(C_1-C_7)$alkylcarbonyl, $(C_1-C_7)$alkoxycarbonyl or $(C_6-C_{12})$aryl.

The [aryl] in this invention is an organic radical derived from aromatic hydrocarbon by eliminating one H, in which each ring of single or fused ring system contains 6-12, preferably 6-10 cyclic atoms. Precisely, it includes phenyl, naphthyl, biphenyl, and indenyl, but not always limited thereto.

The [heteroaryl] in this invention indicates an aryl group which contains 14 hetero atoms selected from the group consisting of N, O and S as aromatic ring structural atoms and the remaining aromatic ring structural atom is C, which is exemplified by 5-6 monocyclic heteroaryl and polycyclic heteroaryl condensed with one or more benzene rings that can be partially saturated.

The oxazolidinone derivatives with cyclic amidoxime or cyclic amidrazone group of the present invention are selected from the following formula II to formula XI.

[Formula II]
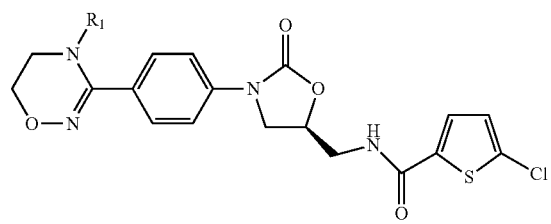

[Formula III]
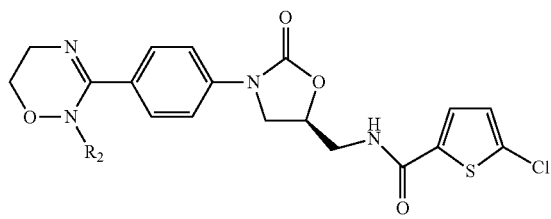

[Formula IV]
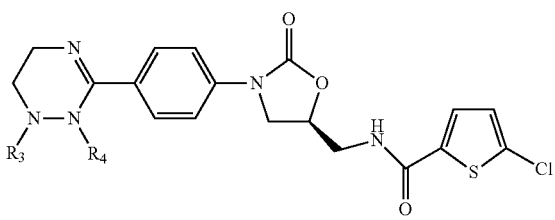

[Formula V]
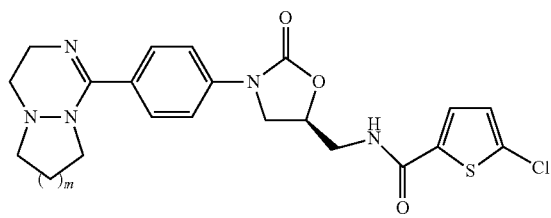

[Formula VI]
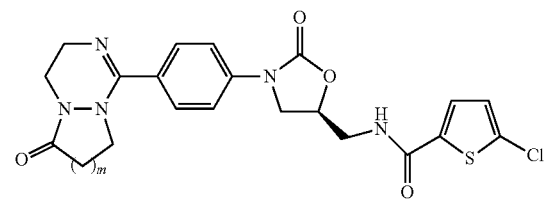

[Formula VII]
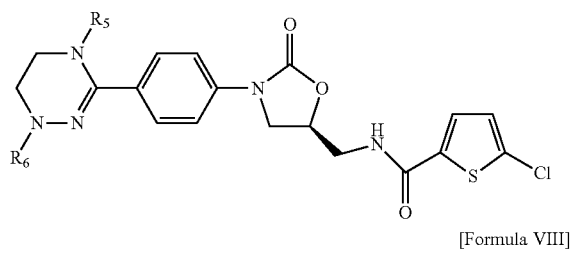

[Formula VIII]
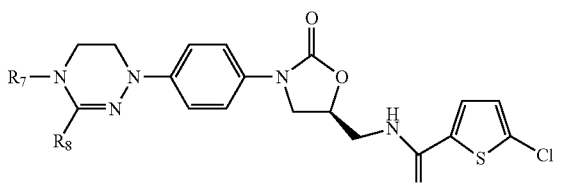

[Formula IX]
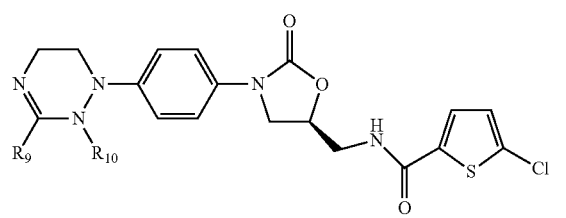

[Formula X]
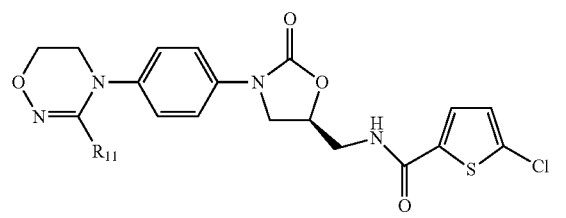

[Formula XI]
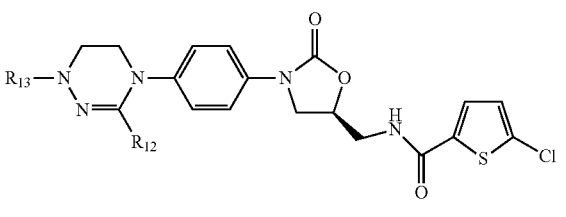

wherein, $R_1$ through $R_{12}$ are independently H, $(C_1-C_7)$ alkyl or $(C_3-C_7)$cycloalkyl; $R_{13}$ is H, $(C_1-C_7)$alkyl, $(C_3-C_7)$ cycloalkyl, formyl or $(C_1-C_7)$alkylcarbonyl; and m is an integer from 1 to 3.

As an example of the oxazolidinone derivatives with cyclic amidoxime or cyclic amidrazone group of the present invention, in the above formula II to formula XI, R1 through R12 are independently H, methyl, ethyl, n-propyl, i-propyl, n-butyl, i-butyl, t-butyl, cyclopropyl, cyclobutyl, cyclopentyl or cyclohexyl; R13 is H, methyl, ethyl, n-propyl, i-propyl, n-butyl, i-butyl, t-butyl, cyclopropyl, cyclobutyl, cyclopentyl, cyclohexyl, formyl or acetyl; and m is an integer of 1.

The oxazolidinone derivatives with cyclic amidoxime or cyclic amidrazone group of the present invention can be exemplified by the following compounds, but not always limited thereto.

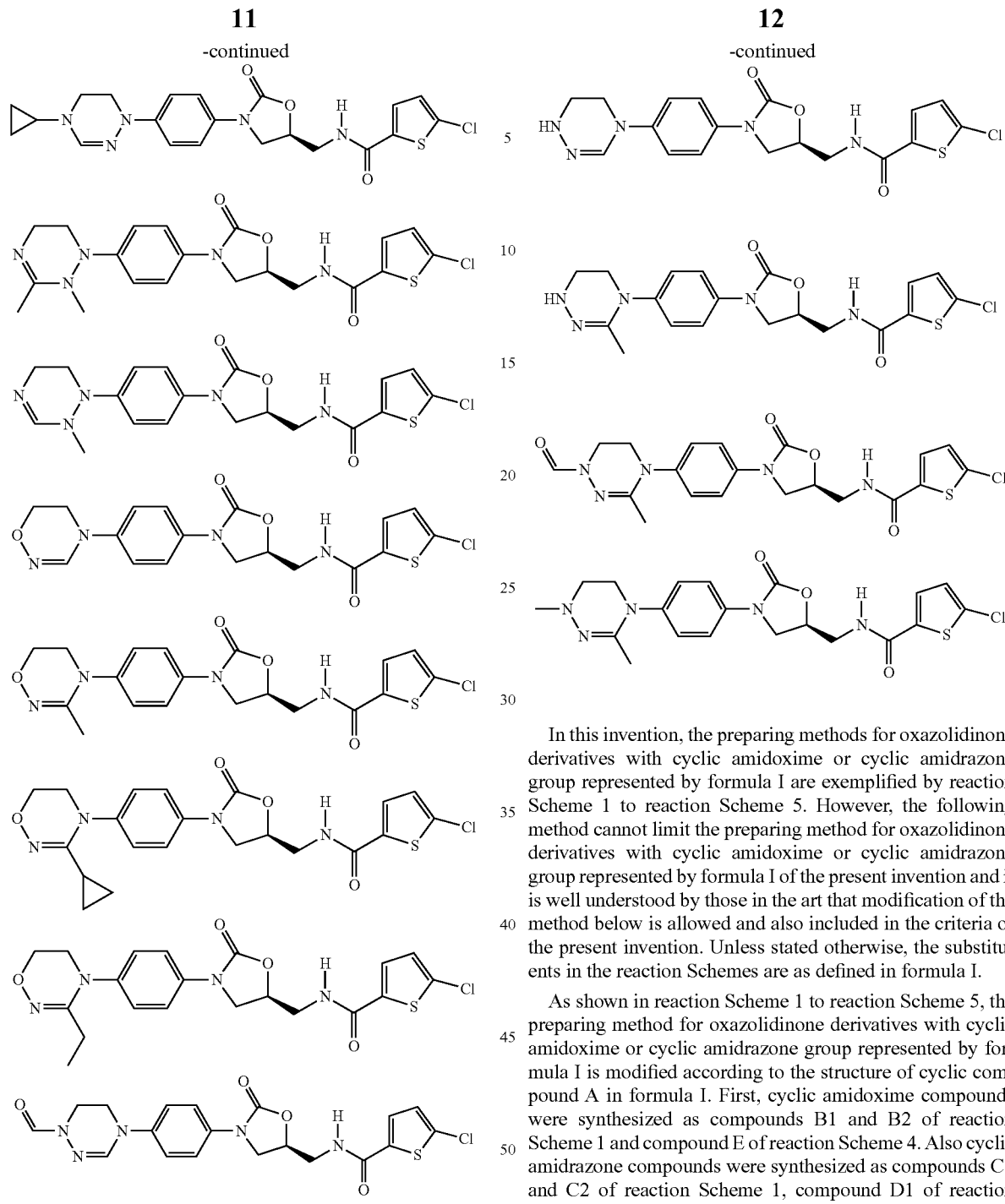

In this invention, the preparing methods for oxazolidinone derivatives with cyclic amidoxime or cyclic amidrazone group represented by formula I are exemplified by reaction Scheme 1 to reaction Scheme 5. However, the following method cannot limit the preparing method for oxazolidinone derivatives with cyclic amidoxime or cyclic amidrazone group represented by formula I of the present invention and it is well understood by those in the art that modification of the method below is allowed and also included in the criteria of the present invention. Unless stated otherwise, the substituents in the reaction Schemes are as defined in formula I.

As shown in reaction Scheme 1 to reaction Scheme 5, the preparing method for oxazolidinone derivatives with cyclic amidoxime or cyclic amidrazone group represented by formula I is modified according to the structure of cyclic compound A in formula I. First, cyclic amidoxime compounds were synthesized as compounds B1 and B2 of reaction Scheme 1 and compound E of reaction Scheme 4. Also cyclic amidrazone compounds were synthesized as compounds C1 and C2 of reaction Scheme 1, compound D1 of reaction Scheme 2 and compound F of reaction Scheme 5.

[Reaction Scheme 1]

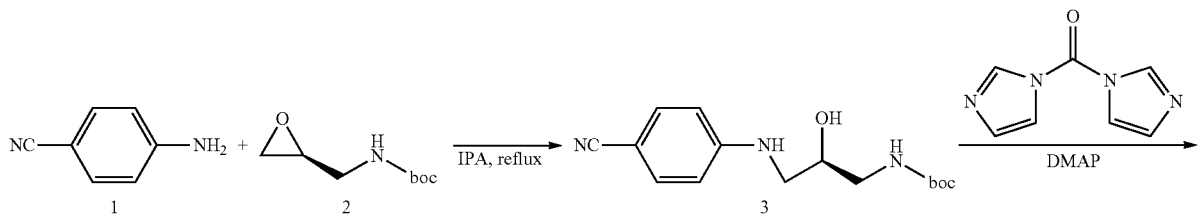

-continued

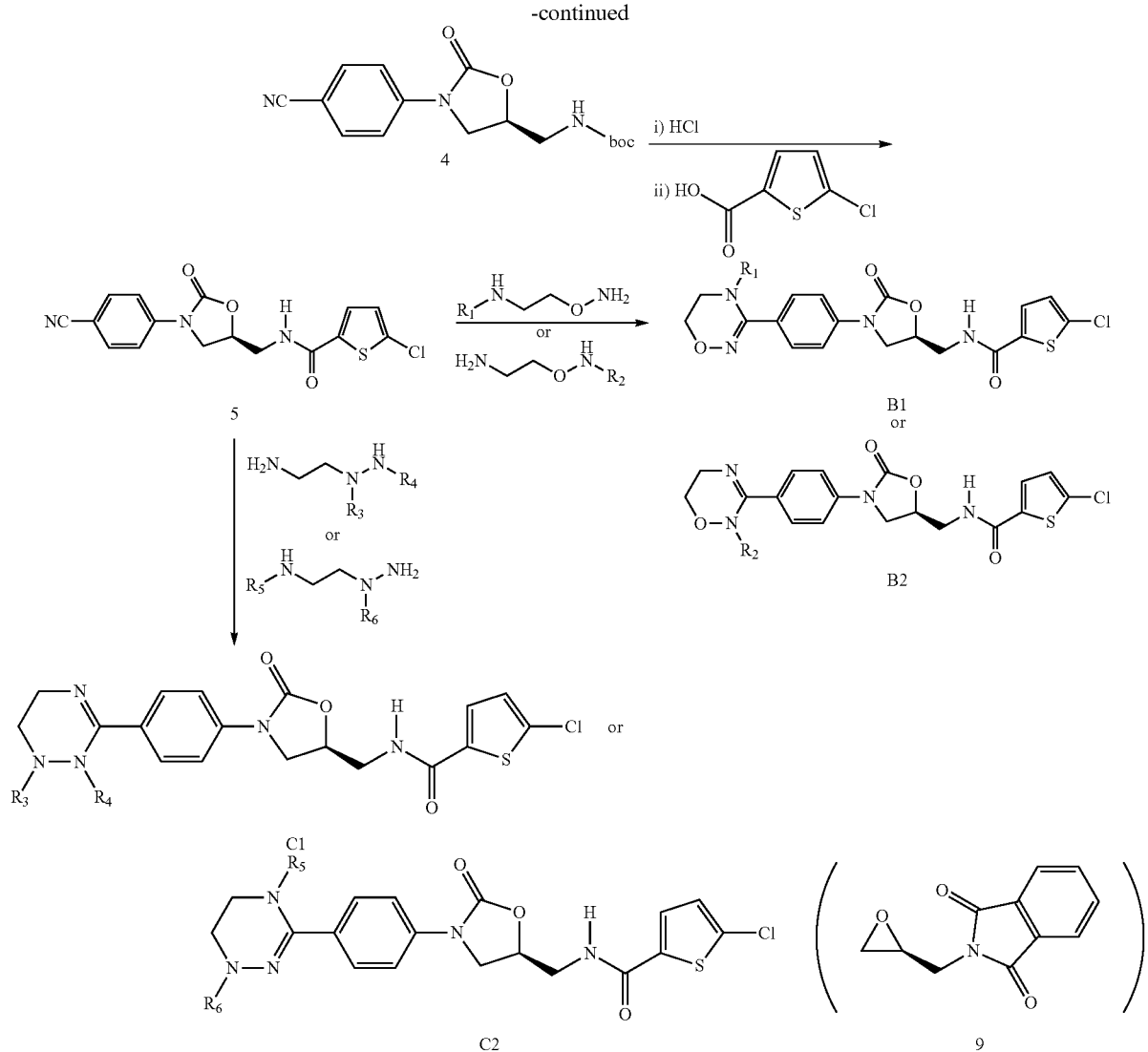

As shown in reaction Scheme 1, synthesis of cyclic amidoxime compounds B1 and B2 of formula I and cyclic amidrazone compounds C1 and C2 was performed by reacting 4-cyanoaniline (1) and 2-(((S)-oxirane-2-nyl)methyl)tert-butyloxycarbonyl (2) to give compound 3. Then, oxazolidinone cyclic compound 4 was synthesized by using 1,1-carbonyldiimidazole and DMAP, which was treated with HCl to eliminate boc protection group. Condensation was performed with 5-chlorothiophene-2-carboxylic acid, followed by treatment with HCl. Finally, the reactant was reacted with diamine compound to give cyclic amidoxime compounds B1 and B2 of formula I and cyclic amidrazone compounds C1 and C2.

In synthesis of compound 3, amine compound protected by phthalimide can be produced by using 2-(((S)-oxirane-2-yl)methyl)isoindoline-1,3-dione (9) of reaction Scheme 2 instead of 2-(((S)-oxirane-2-nyl)methyl)tert-butyloxycarbonyl (2), similarly with the process of reaction Scheme 2. In reaction Scheme 1, process using 2-(((S)-oxirane-2-nyl)methyl)tert-butyloxycarbonyl (2) is described and in reaction Scheme 2, process using 2-(((S)-oxirane-2-yl)methyl)isoindoline-1,3-dione (9) is described.

Cyclic amidrazone compounds D1 and D2 of formula I can be divided by the location of double bond and are synthesized by reaction Scheme 2 and reaction Scheme 3.

[Reaction Scheme 2]

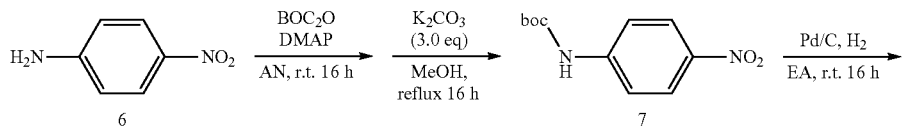

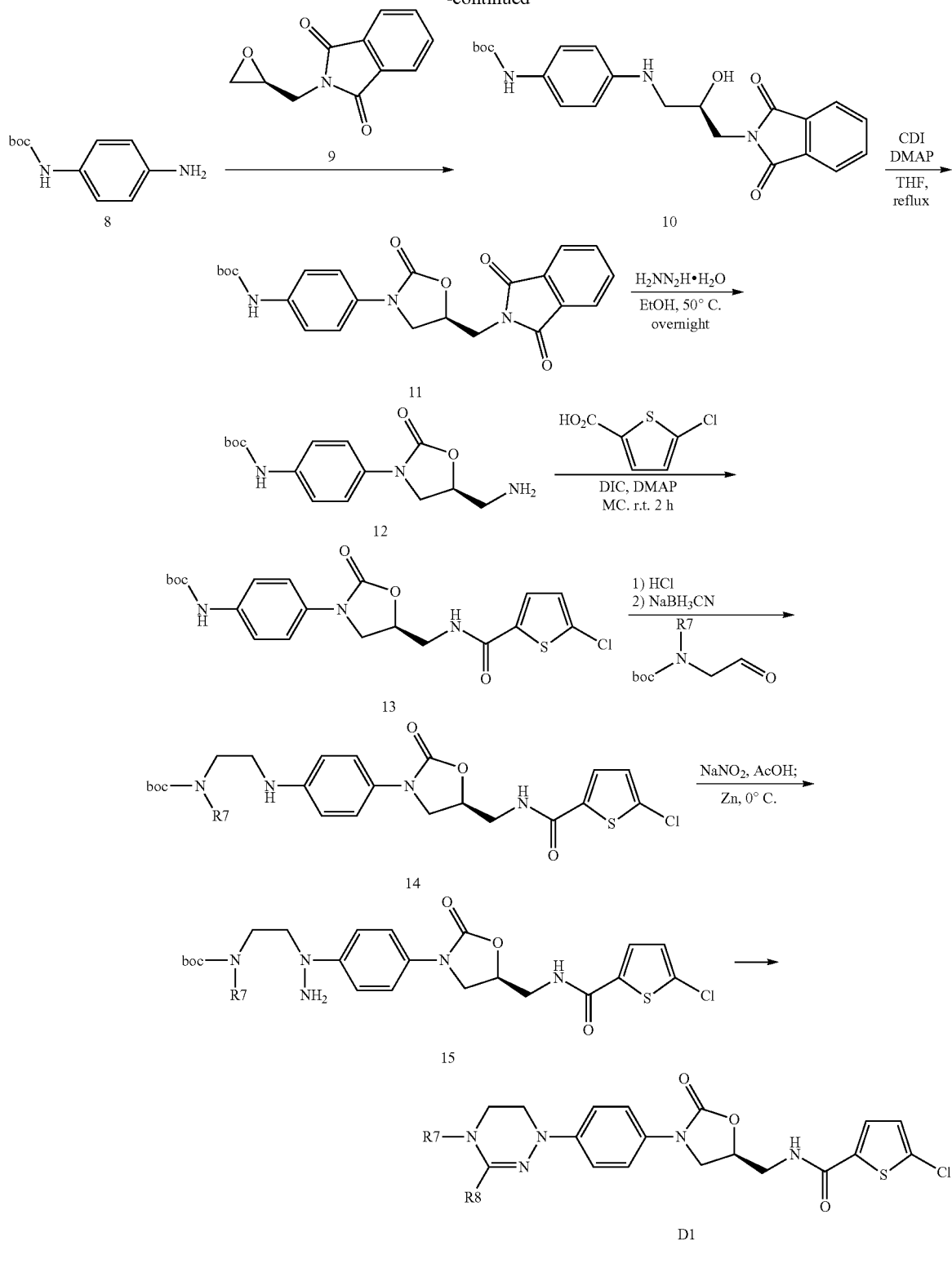

First, 4-nitroaniline (6) was protected with boc group, followed by hydrogenation using palladium catalyst. Then, aminoalcohol compound 10 was synthesized by using 2-(((S)-oxirane-2-yl)methyl)isoindoline-1,3-dione (9). Oxazolidinone ring was made by using carbonyldiimidazole to give compound II. Phthalimide protection group was eliminated by hydrazine, followed by condensation with 5-chlorothiophene-2-carboxylic acid to give compound 13. Compound 13 was treated with HCl to eliminate boc protection group, followed by reaction with boc protected aminal to give compound 14. Nitroso group was introduced using $NaNO_2$, followed by reduction with Zn to give hydrazine compound 15. Compound 15 was reacted with ortho-formate to give cyclic amidrazone compound D1.

Another cyclic amidrazone compound D2 was synthesized by reaction Scheme 3.

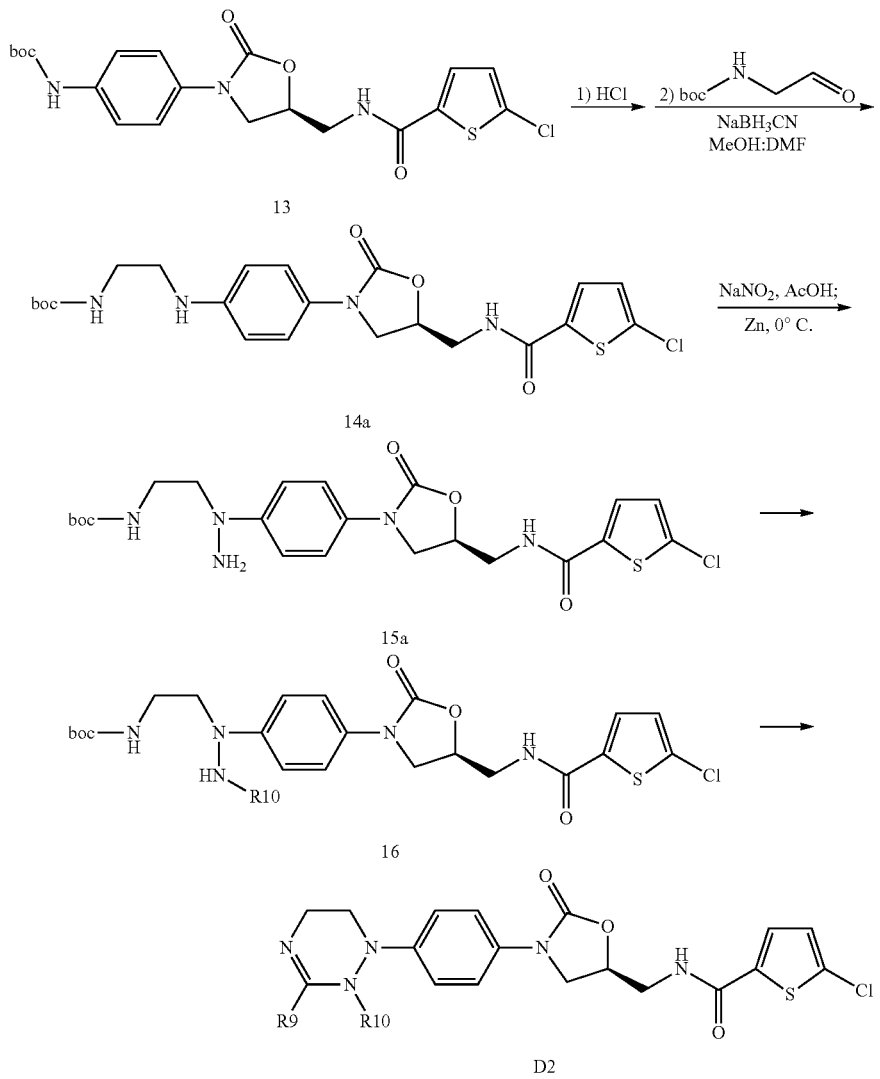

From the compound 14 shown in reaction Scheme 2, compound 14a in which $R_7$ was H was synthesized, to which amino group was introduced (15a) and then alkyl group was introduced stepwise (16). Cyclization was induced using ortho-formate to give cyclic amidrazone compound D2.

Cyclic amidoxime compound E of formula I was synthesized by reaction Scheme 4.

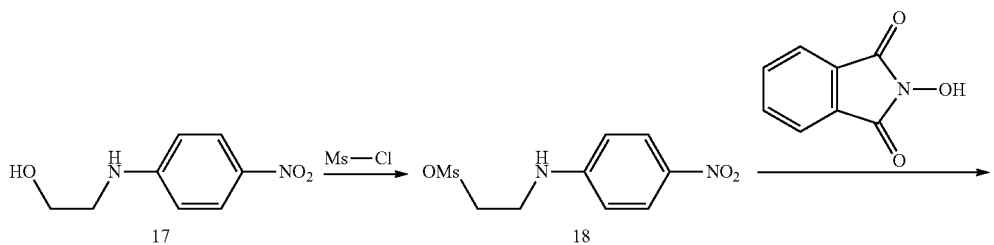

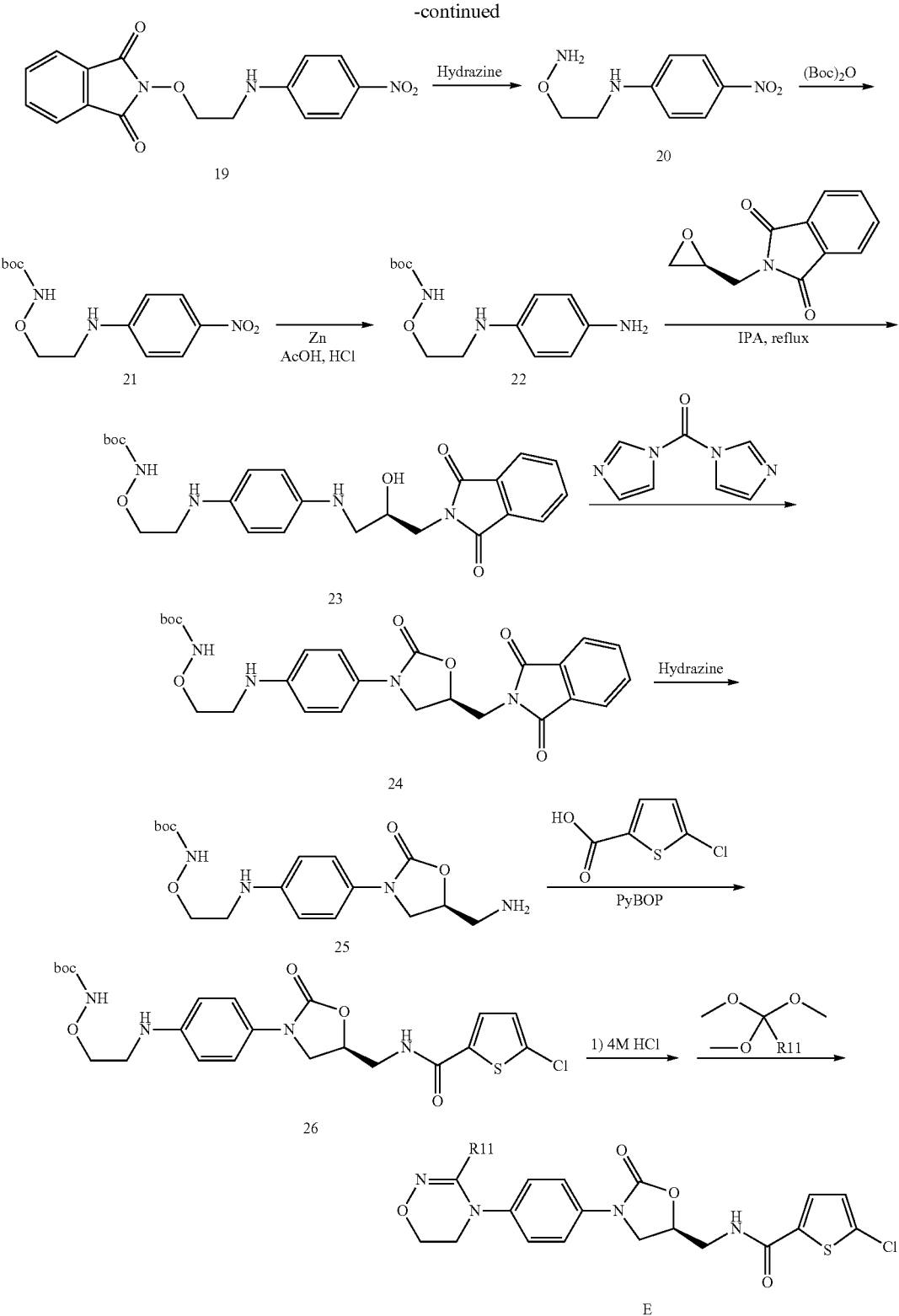

Compound 17 produced from 4-fluoronitrobenzene was reacted with methanesulfonyl chloride to give compound 18, followed by reaction with hydroxyphthalimide to give compound 19. Phthalimide protection group was eliminated by hydrazine, but boc group was used to protect instead, resulting in compound 21. Nitro group of compound 21 was reduced using Zn to give compound 22, followed by reaction with 2-(((S)-oxirane-2-yl)methyl)isoindoline-1,3-dione (9) by the process shown in reaction Scheme 2 to give compound 26. Compound 26 was treated with HCl, followed by reaction with ortho-ester to give compound E.

Cyclic amidrazone compound F of formula I was synthesized by reaction Scheme 5.
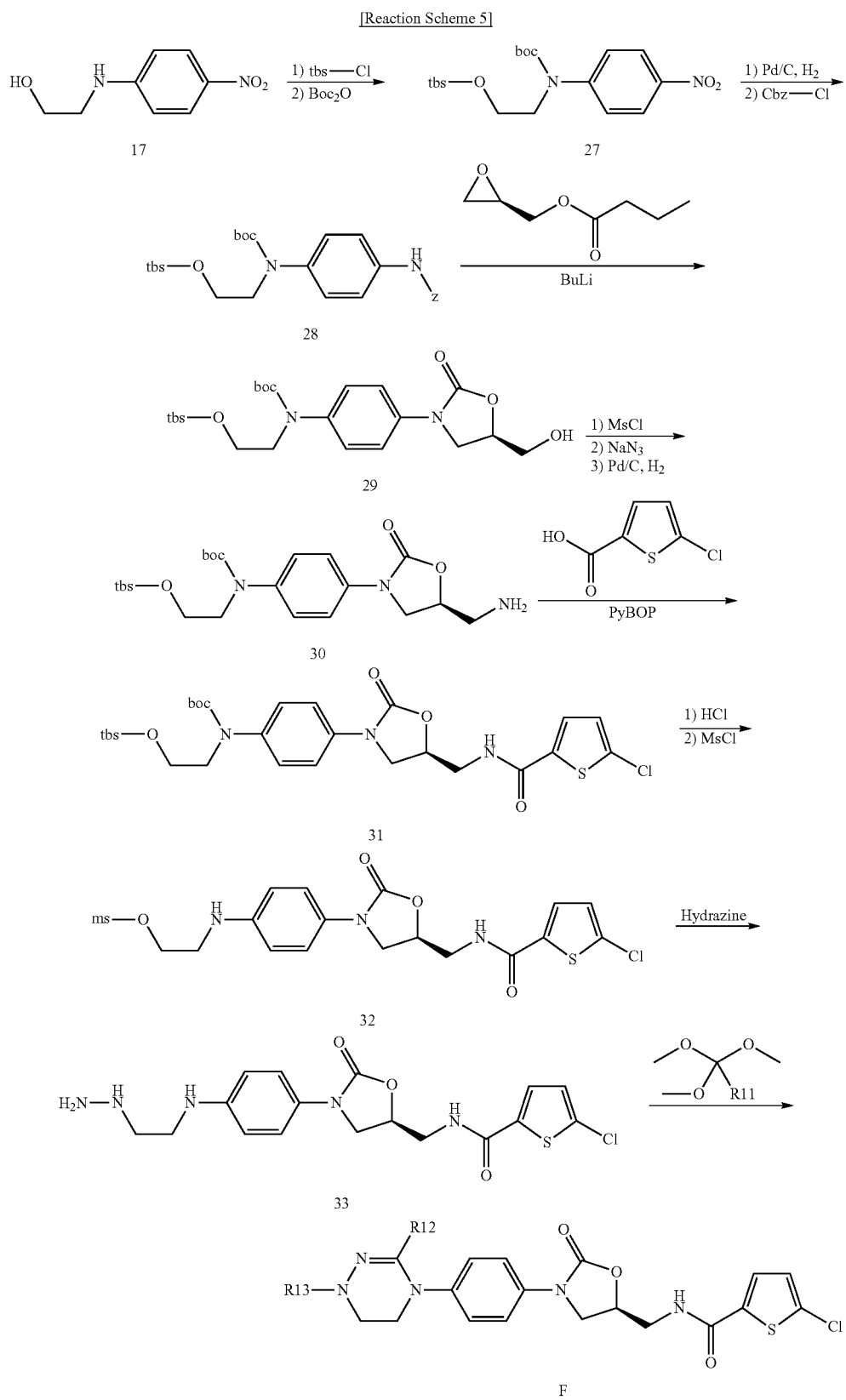
[Reaction Scheme 5]

Compound 17 produced from 4-fluoronitrobenzene was protected with tbs (tert-butyldimethylsilyl) group and then amine region was protected with boc, resulting in compound 27. Amine was prepared by using palladium catalyst, which was reacted with Cbz-Cl to give compound 28. Compound 28 was reacted with glycidylbutylate to give compound 29. Alcohol group was replaced with amine to give compound 30. This compound was reacted with chlorothiophene carboxylic acid to give compound 31, followed by reaction with methanesulfonyl chloride. The reactant was treated with hydrazine to give compound 33. Compound 33 was reacted with orthoester to give compound F.

The oxazolidinone derivatives with cyclic amidoxime or cyclic amidrazone group represented by formula I of the present invention can be used as a pharmaceutically active ingredient for the prevention and treatment of, in particular, thrombosis, myocardial infarction, arteriosclerosis, inflammatory, apoplexy, angina pectoris, recurrent stricture after angioplasty, intermittent claudication, phlebothrombosis, pulmonary embolism, arterial thrombosis, myocardial ischemia, unstable angina based on thrombosis, and thromboembolism such as crisis in a medicine The oxazolidinone derivatives with cyclic amidoxime or cyclic amidrazone group represented by formula I of the present invention or the pharmaceutically acceptable salts thereof can be used for the prevention or treatment of atherosclerotic disease including coronary artery disease, cerebral artery disease or peripheral artery disease. To treat myocardial infarction, the oxazolidinone derivatives with cyclic amidoxime or cyclic amidrazone group can be co-used with a thrombolytic agent (for example, alteplase, tenecteplase, etc). The said compounds can also be used for the prevention of reocclusion after thrombolysis, percutaneous transluminal coronary angioplasty (PTCA) and coronary artery bypass.

The oxazolidinone derivatives with cyclic amidoxime or cyclic amidrazone group represented by formula I of the present invention or the pharmaceutically acceptable salts thereof can be used for the prevention of post-surgery thrombus reformation. It can also be used as an anticoagulant in relation to artificial organ or hemodialysis. The said compound can be used for washing catheter and medical assist device used in vivo. In addition, it can also be used as an anticoagulant composition for ex vivo storage of blood, plasma and other types of blood products. The said compounds of the present invention are also effective in the treatment of blood coagulation related disease or disease causing secondary lesion such as cancer (including metastatic cancer), inflammatory disease including arthritis and diabetes.

The oxazolidinone derivatives with cyclic amidoxime or cyclic amidrazone group represented by formula I of the present invention can be used in the form of pharmaceutically acceptable salts. As for the pharmaceutically acceptable salts, it is preferably an acid addition salt prepared by using a pharmaceutically acceptable free acid. Whether it is inorganic or organic, a free acid can be used if it is pharmaceutically acceptable. Examples of the inorganic free acid include hydrochloric acid, hydrobromic acid, sulfuric acid, and phosphoric acid. Available organic free acids are exemplified by citric acid, acetic acid, lactic acid, maleic acid, fumaric acid, gluconic acid, methanesulfonic acid, glycolic acid, succinic acid, 4-toluenesulfonic acid, trifluoroacetic acid, galacturonic acid, embonic acid, glutamic acid and aspartic acid. The oxazolidinone derivatives of the present invention can contain hydrate of the salt. In particular, if the said salt has hygroscopicity, it is preferably used in the form of crystalline hydrate.

The oxazolidinone derivatives with cyclic amidoxime or cyclic amidrazone group represented by formula I of the present invention can be formulated as a prodrug designed to increase in vivo absorptiveness or solubility and can be used in the form of hydrate or solvate. For example, as explained below, a group that can be easily separated after in vivo absorption is attached or the compound is prepared in the form of salt, precisely in the form of one or more hydrates or solvates. The prodrug and hydrate or solvate of the salt are also included in the criteria of the present invention.

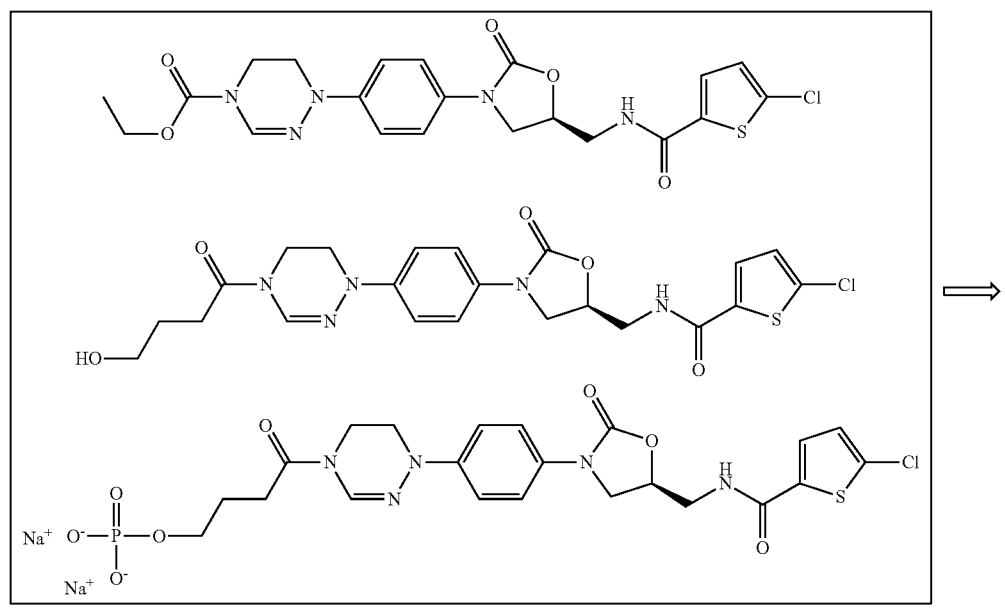

Prodrug

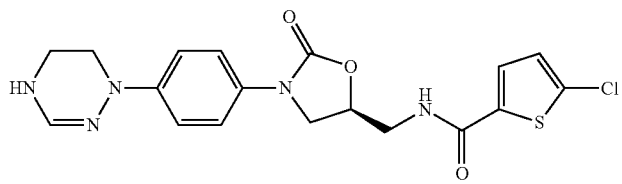

The effective dosage of the oxazolidinone derivatives represented by formula I, its hydrates, its solvates or its pharmaceutically acceptable salts can be determined by considering specific compounds used, administration method, target subject, target disease, etc, to bring treatment effect, but 0.1-20 mg/kg (body weight) per day is preferred dose of the oxazolidinone derivative compound represented by formula I. The daily dose can be administered once a day (at a time) or a few times a day as divided properly within a daily effective dose. According to formulation, oral administration, parenteral administration (injection) or local administration can be allowed. The pharmaceutical composition of the present invention can be formulated for oral administration such as tablets, powders, dry syrups, chewable tablets, granules, capsules, soft capsules, pills, drinks, sublinguals, etc. The composition of the invention formulated as tablets can be administered to a subject by any method or pathway that delivers the effective dose of the tablet with bioavailability, which can be oral pathway. Also the administration method or pathway can be determined according to the characteristics, stages of the target disease and other conditions. When the composition of the invention is formed as tablets, it can additionally include pharmaceutically acceptable excipients. The content and characteristics of the excipient can be determined by solubility and chemical properties of the selected tablet, administration pathway and standard pharmaceutical practice.

BRIEF DESCRIPTION OF DRAWINGS

The above and other objects, features and advantages of the present invention will become apparent from the following description of preferred embodiments given in conjunction with the accompanying drawings, in which:

FIG. 1 is a diagram showing the mechanism of blood coagulation.

MODE FOR THE INVENTION

Practical and presently preferred embodiments of the present invention are illustrative as shown in the following Examples.

Manufacturing Example 1

Preparation of Compound 5

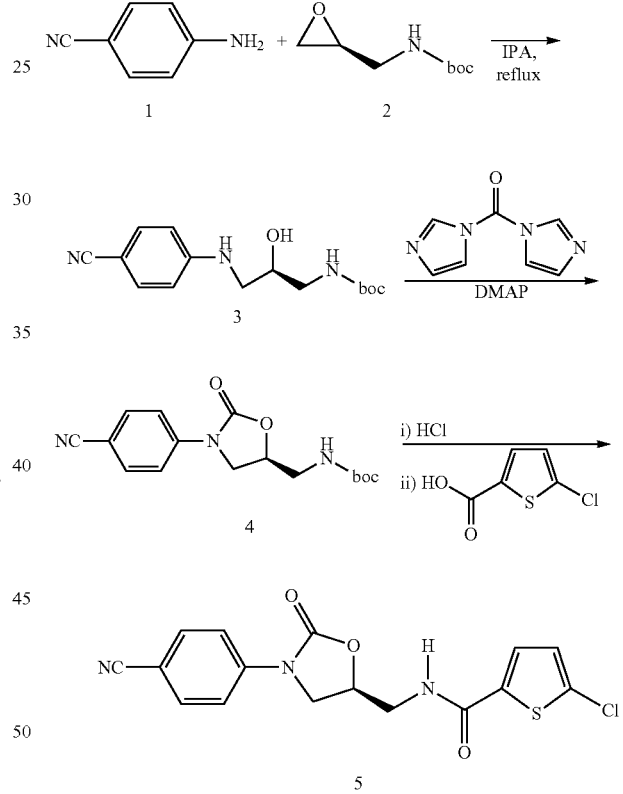

<1-1> Preparation of Compound 3

4-aminobenzonitrile(1) (5 g, 42.30 mmol) and 2-(((S)-oxirane-2-nyl)methyl)tert-butyloxycarbonyl (2) (8.79 g, 50.78 mmol) were added to 2-isopropylalcohol (20 mL), followed by reflux with stirring for 12 hours. The reactant was concentrated under reduced pressure, and then proceeded to column to give the titled compound 3 as a white solid (7.30 g, 25.1 mmol, 59%).

$^1$H NMR (400 MHz, chloroform-$d_1$) δ=7.41 (d, J=8.4 Hz, 4H), 6.59 (d, J=8.4 Hz, 1H), 4.95 (br s, 1H), 4.80 (br s, 1H), 3.97-3.93 (m, 1H), 3.31-3.15 (m, 5H), 1.46 (s, 9H)

<1-2> Preparation of Compound 4

Compound 3 obtained above (7.30 g, 25.05 mmol), 1,1-carbonyldiimidazole (4.87 g, 30.06 mmol) and dimethylaminopyridine (1.53 g, 12.52 mmol) were added to tetrahydrofurane (70 mL) stepwise, followed by reflux with stirring for 12 hours. The reactant was concentrated under reduced pressure, which was then dissolved in ethyl acetate (300 mL). After washing with 1N-HCl solution (50 mL) and sodium bicarbonate solution (50 mL) stepwise, the reactant was dried over sodium sulfate, followed by concentration under reduced pressure. The reactant was washed with diethylether (100 mL) to give compound 4 as a white solid (6.60 g, 20.8 mmol, 83%).

$^1$H NMR (400 MHz, chloroform-$d_1$) δ=7.67 (s, 4H), 4.95 (br s, 1H), 4.82-4.79 (m, 1H), 4.07 (dd, J=8.8, 8.8 Hz, 1H), 3.94 (dd, J=8.8, 6.8 Hz, 1H), 3.56-3.54 (m, 2H), 1.38 (s, 9H)

<1-3> Preparation of Compound 5

The compound 4 obtained above (6 g, 18.90 mmol) was added to ethyl acetate (10 mL), which was added to 4N-HCl dissolved in 1,4-dioxane (60 mL), followed by stirring at room temperature for one hour. The generated solid was filtered under reduced pressure and then washed with ethyl acetate (20 mL) and diethylether (30 mL) stepwise. As a result, hydrochloride of amine compound excluding boc was obtained as a white solid (4.60 g, 18.1 mmol, 95.9%).

$^1$H NMR (400 MHz, chloroform-$d_1$) δ=8.36 (br s, 3H), 7.90 (d, J=8.8 Hz, 2H), 7.73 (d, J=8.8 Hz, 2H), 5.03-4.96 (m, H), 4.25 (dd, J=9.2, 9.2 Hz, 1H), 3.92 (dd, J=9.2, 6.4 Hz, 1H), 3.28-3.25 (m, 2H)

The amine compound (4.60 g, 18.13 mmol), HOBt (2.75 g, 19.94 mmol), EDC (4.17 g, 21.75 mmol), 5-chlorothiophene-2-carboxylic acid (3.20 g, 19.04 mmol), and triethylamine (5.70 mL, 39.88 mmol) were added to N,N-dimethylformamide (50 mL) stepwise, followed by stirring at room temperature for 12 hours. The reactant was slowly added to distilled water (800 mL) and the generated solid was filtered under reduced pressure. The reactant was washed with diethylether (100 mL) to give compound 5 as a white solid (5.70 g, 15.8 mmol, 87%).

$^1$H NMR (400 MHz, DMSO-$d_6$) δ=8.93 (t, J=5.2 Hz, 1H), 7.81 (d, J=9.2 Hz, 2H), 7.69 (d, J=9.2 Hz, 2H), 7.63 (d, J=4.0 Hz, 1H), 7.15 (d, J=4.0 Hz, 1H), 4.86-4.81 (m, 1H), 4.17 (dd, J=9.2, 9.2 Hz, 1H), 3.83 (dd, J=9.2, 5.2 Hz, 1H), 3.57 (dd, J=5.2, 5.2 Hz, 2H); LCMS: 362 (M+H$^+$) to $C_{16}H_{12}ClN_3O_3S$

Manufacturing Example 2

Preparation of Compound 13

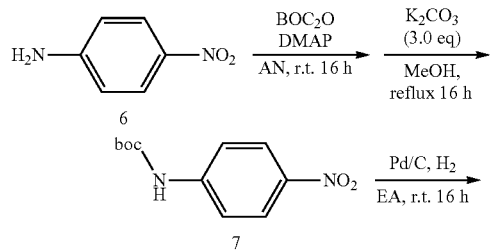

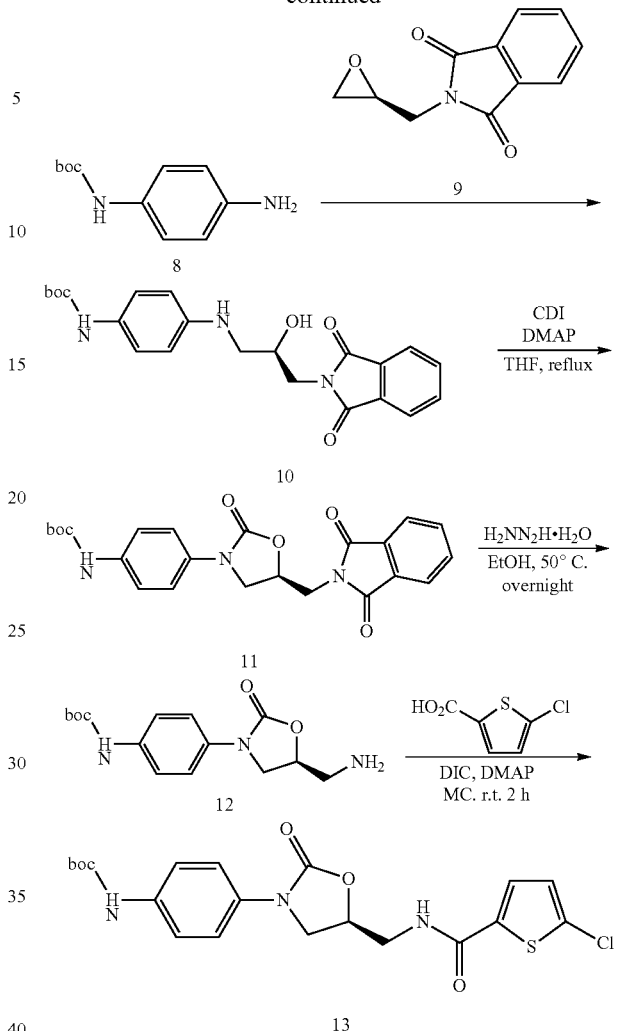

<2-1> Preparation of Compound 7

4-nitroaniline (20 g, 145 mmol) was dissolved in acetonitrile (200 mL), to which di t-butyl dicarbonate (63.2 g, 290 mmol) and 4-dimethylaminopyridine (3.54 g, 29 mmol) were added, followed by reflux with stirring for 16 hours. The reaction solution was cooled down at room temperature, followed by concentration under reduced pressure to give brown solid compound having two boc groups (49 g, 145 mmol, 100%).

$^1$H NMR (600 MHz, CDCl$_3$) δ=8.25 (d, J=9 Hz, 2H), 7.36 (d, J=9 Hz, 2H), 1.45 (s, 18H)

The obtained compound (49 g, 145 mmol) was dissolved in methanol (200 mL), to which potassium carbonate (60 g, 434 mmol) was added, followed by reflux with stirring for 16 hours. The reaction solution was cooled down at room temperature, followed by concentration under reduced pressure. Column chromatography (n-hexane/ethyl acetate, 6/1) with the reaction solution was performed to give the title compound 7 as a light yellow solid (17.6 g, 73.9 mmol, 51%).

$^1$H NMR (600 MHz, CDCl$_3$) δ=8.18 (d, J=9 Hz, 2H), 7.53 (d, J=9 Hz, 2H), 6.93 (br s, 1H), 1.54 (s, 9H)

<2-2> Preparation of Compound 8

Compound 7 (17.6 g, 73.9 mmol) was dissolved in ethyl acetate (200 mL), to which palladium/charcoal (10 wt %, 3.9 g) was added, followed by stirring in hydrogen balloon. 16 hours later, the reaction solution was filtered through sellaite, followed by concentration under reduced pressure to give the title compound 8 as a light pink solid (15.4 g, 73.9 mmol, 100%).

$^1$H NMR (600 MHz, CDCl$_3$) δ=7.12 (br s, 2H), 6.62 (d, J=9 Hz, 2H), 6.31 (br s, 1H), 3.53 (br s, 2H), 1.50 (s, 9H)

<2-3> Preparation of Compound 10

Compound 8 (13.5 g, 65.1 mmol) was dissolved in 2-propanol (170 mL), to which (S)-glycidyl phthalimide (9) (14.6 g, 71.9 mmol) was added, followed by reaction for 12 hours. Then, (S)-glycidyl phthalimide (9) (2.65 g, 13.0 mmol) was additionally added, followed by reflux with stirring for 4 hours. The reaction solution was cooled down at room temperature and then concentrated under reduced pressure. Recrystallization was performed with n-hexane (500 mL) to give the title compound 10 as a yellow solid (26.8 g, 65.1 mmol, 100%).

$^1$H NMR (600 MHz, CDCl$_3$) δ=7.89-7.84 (m, 2H), 7.78-7.73 (m, 2H), 7.15 (br, 2H), 6.63 (d, J=8 Hz, 2H), 6.26 (br, 1H), 4.18-4.12 (m, 1H), 4.05 (br, 1H), 3.94-3.86 (m, 2H), 3.25 (dd, J=13, 4.5 Hz, 1H), 3.15 (dd, J=13, 6.6 Hz, 1H), 2.84 (d, J=4.8 Hz, 1H), 1.50 (s, 9H)

<2-4> Preparation of Compound 11

Compound 10 (26.8 g, 65.1 mmol) was dissolved in tetrahydrofurane (200 mL), to which 1,1-carbonyldiimidazole (15.9 g, 98.1 mmol) and 4-dimethylaminopyridine (1.59 g, 13.0 mmol) were added, followed by reflux with stirring for 16 hours. The reaction solution was cooled down and concentrated under reduced pressure. Saturated ammonium chloride solution (200 mL) was added thereto, followed by extraction with ethyl acetate (250 mL×2). The collected organic layer was dried over anhydrous sodium sulfate, filtered, concentrated under reduced pressure and then proceeded to column chromatography (n-hexane/ethyl acetate/dichloromethane, 1/1/1) to give the titled compound II as a light yellow solid (20.0 g, 45.7 mmol, 70%).

$^1$H NMR (600 MHz, CDCl$_3$) δ=7.91-7.87 (m, 2H), 7.79-7.74 (m, 2H), 7.43 (d, J=9 Hz, 2H), 7.36 (d, J=9 Hz, 2H), 6.48 (br s, 1H), 5.00-4.95 (m, 1H), 4.15 (dd, J=14, 7 Hz, 1H), 4.11 (t, J=9 Hz, 1H), 3.97 (dd, J=14, 6 Hz, 1H), 3.89 (dd, J=9, 6 Hz, 1H), 1.52 (s, 9H)

<2-5> Preparation of Compound 12

Compound II (15.3 g, 35.0 mmol) was dissolved in ethanol (200 mL), to which hydrazine hydrate (3.40 mL, 70.0 mmol) was added, followed by reflux with stirring for 3 hours. The reaction solution was cooled down at room temperature. The generated white solid was filtered out and the filtrate was concentrated under reduced pressure. Dichloromethane (100 mL) was added thereto and then the generated solid was eliminated by filtration. The filtrate was concentrated under reduced pressure. This process was repeated twice more and then the reactant was dried to give the title compound 12 as a white solid (10.0 g, 32.5 mmol, 93%).

$^1$H NMR (600 MHz, CDCl$_3$) δ=7.45 (d, J=9 Hz, 2H), 7.37 (d, J=9 Hz, 2H), 6.65 (br s, 1H), 4.67-4.63 (m, 1H), 4.03 (t, J=9 Hz, 1H), 3.82 (dd, J=9, 7 Hz, 1H), 3.09 (dd, J=14, 4 Hz, 1H), 2.98 (dd, J=14, 6 Hz, 1H), 1.52 (s, 9H)

<2-6> Preparation of Compound 13

Compound 12 (3.63 g, 11.8 mmol) was dissolved in chloroform (50 mL), to which 5-chlorothiophenecarboxylic acid (2.30 g, 14.1 mmol) and 4-dimethylaminopyridine (0.30 g, 13.0 mmol) were added. Temperature was lowered to 0° C. N,N'-diisopropylcarbodiimide (2.20 mL, 14.1 mmol) was added thereto, followed by stirring at room temperature for 2 hours. The reaction solution was concentrated under reduced pressure, followed by re-crystallization in n-hexane/diethyl-ether solution (1/1, 200 mL) to give the titled compound 13 as a white solid (5.0 g, 11.1 mmol, 94%).

$^1$H NMR (400 MHz, DMSO-d$_6$) δ=9.30 (s, 1H), 8.95 (t, J=6 Hz, 1H), 7.67 (d, J=4 Hz, 1H), 7.45-7.36 (m, 4H), 7.17 (d, J=4 Hz, 1H), 4.82-4.74 (m, 1H), 4.11 (t, J=9 Hz, 1H), 3.77 (dd, J=9, 6 Hz, 1H), 3.57 (t, J=5.6 Hz, 2H), 1.45 (s, 9H)

Manufacturing Example 3

Preparation of Compound 16a

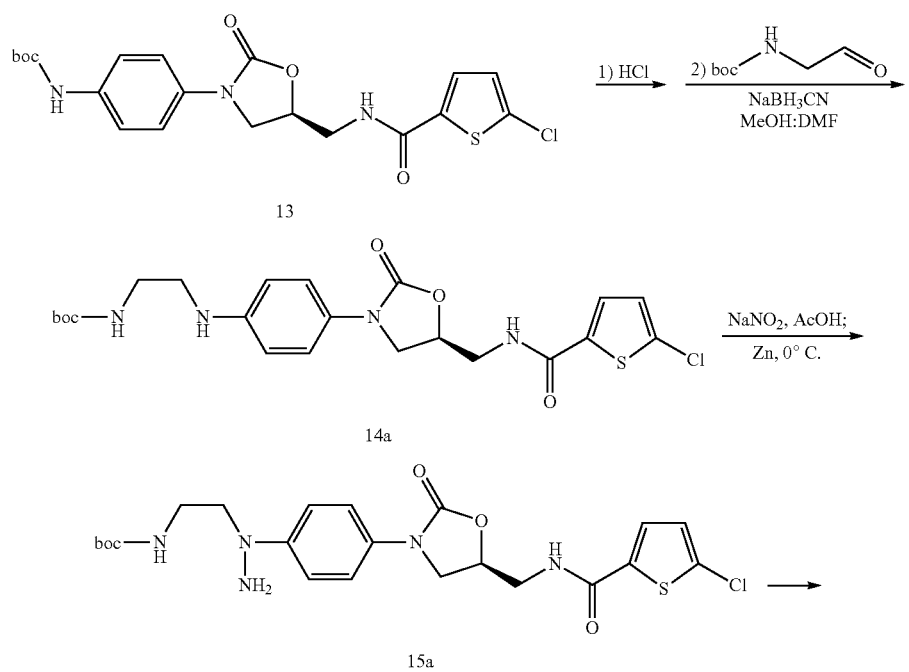

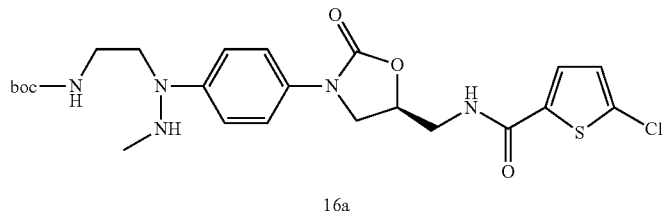

16a

<3-1> Preparation of Compound 14a

Compound 13 (16.5 g, 36.5 mmol) was dissolved in dichloromethane (150 mL), to which HCl (150 mL, 4 M 1,4-dioxane solution) was added, followed by stirring at room temperature for 1 hour. The reaction solution was concentrated under reduced pressure and dried to give white solid compound (14.1 g, 36.3 mmol, 99%).

$^1$H NMR (600 MHz, DMSO-$d_6$) δ=9.07 (t, J=6 Hz, 1H), 7.73 (d, J=3.6 Hz, 1H), 7.63 (d, J=9 Hz, 2H), 7.37 (d, J=9 Hz, 2H), 7.20 (d, J=3.6 Hz, 1H), 4.88-4.83 (m, 1H), 4.18 (t, J=9 Hz, 1H), 3.87 (dd, J=9, 6 Hz, 1H), 3.61 (t, J=5.4 Hz, 2H)

Methanol (40 mL) and N,N-dimethylformamide (15 mL) were added to the compound obtained above (3.0 g, 7.73 mmol), to which N-Boc-2-aminoacetaldehyde (1.48 g, 9.30 mmol) and sodium cyanoborohydride (486 mg, 7.73 mmol) were added, followed by stirring at room temperature for 16 hours. Saturated ammonium chloride solution (20 mL) was added thereto, and then the solvent was concentrated under reduced pressure. Saturated ammonium chloride solution (50 mL) was added thereto again, followed by extraction with ethyl acetate (250 mL×2). The collected organic layer was dried over anhydrous sodium sulfate, filtered, concentrated under reduced pressure and then proceeded to column chromatography (n-hexane/ethyl acetate, 1/2→1/4) to give the titled compound 14a as a white solid (2.76 g, 5.58 mmol, 72%).

$^1$H NMR (400 MHz, CDCl$_3$) δ=7.30 (d, J=4 Hz, 1H), 7.18 (d, J=9 Hz, 2H), 7.00 (t, J=6 Hz, 1H), 6.80 (d, J=4 Hz, 1H), 6.53 (d, J=9 Hz, 2H), 4.84-4.74 (m, 2H), 4.04 (br, 1H), 3.98 (t, J=9 Hz, 1H), 3.81 (ddd, J=14.4, 6, 3 Hz, 1H), 3.74 (dd, J=9, 6 Hz, 1H), 3.66 (dt, J=14.8, 9 Hz, 1H), 3.36-3.26 (m, 2H), 3.18 (t, J=6 Hz, 2H), 1.41 (s, 9H)

<3-2> Preparation of Compound 15a

Compound 14a (1.0 g, 2.0 mmol) was dissolved in acetic acid (10 mL), to which sodium nitrate (NaNO$_2$) (170 mg, 2.46 mmol) dissolved in distilled water (2 mL) was slowly loaded at 0° C., followed by stirring for 30 minutes. Then, zinc amalgam (650 mg of zinc was washed with 0.5% mercury (II) acetate solution and then washed with distilled water, which was used rightly) was loaded thereto, followed by stirring at 0° C. for 5 hours. Saturated sodium carbonate solution (50 mL) was slowly added thereto, followed by extraction with ethyl acetate (250 mL×2). The collected organic layer was dried over anhydrous sodium sulfate, filtered, concentrated under reduced pressure and then proceeded to column chromatography (n-hexane/ethyl acetate, 1/2→1/4) to give the titled compound 15a as a light yellow solid (450 mg, 0.88 mmol, 45%).

$^1$H NMR (600 MHz, CDCl$_3$) δ=7.34 (d, J=3.6 Hz, 1H), 7.32 (d, J=8.4 Hz, 2H), 6.96 (d, J=8.4 Hz, 2H), 6.90 (br, 1H), 6.87 (d, J=3.6 Hz, 1H), 4.94 (br s, 1H), 4.87-4.81 (m, 1H), 4.05 (t, J=9 Hz, 1H), 3.90-3.83 (m, 1H), 3.80 (dd, J=9, 6 Hz, 1H), 3.75-3.67 (m, 1H), 3.68 (br s, 2H), 3.44 (br, 4H), 1.41 (s, 9H)

<3-3> Preparation of Compound 16a

Compound 15a (150 mg, 0.29 mmol) was dissolved in methanol (3 mL), to which formalin (0.10 mL, 37 wt % aqueous solution) was added, followed by stirring at room temperature for 1 hour. The reaction solution was concentrated under reduced pressure and diluted with distilled water (15 mL), followed by extraction with dichloromethane (15 mL×2). The collected organic layer was dried over anhydrous sodium sulfate, filtered, and concentrated under reduced pressure to give 110 mg of light yellow solid. This solid was dissolved in methanol (3 mL) and tetrahydrofurane (1 mL), and then temperature was lowered to 0° C. Sodium borohydride (160 mg, 4.22 mmol) was added thereto. pH was regulated as 5 using acetic acid and reaction temperature was slowly raised to 50° C. 10 hours later, the reaction solution was concentrated under reduced pressure and diluted with 2N HCl solution (30 mL), followed by extraction with dichloromethane (25 mL×2). The collected organic layer was dried over anhydrous sodium sulfate, filtered, concentrated under reduced pressure and then proceeded to column chromatography (n-hexane/ethyl acetate, 1/1→1/3) to give the titled compound 16a as a white solid (15 mg, 0.029 mmol).

Manufacturing Example 4

Preparation of Compound 15b

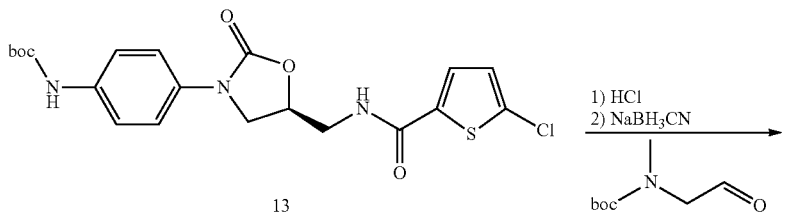

-continued

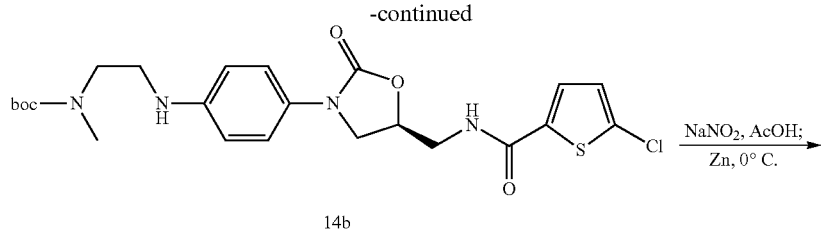

<4-1> Preparation of Compound 14b

As explained in the synthesis of compound 14a in Manufacturing Example 3, compound 13 was dissolved in dichloromethane, to which HCl (4 M 1,4-dioxane solution) was added, followed by stirring at room temperature for 1 hour. The reaction solution was concentrated under reduced pressure and dried to give white solid compound (500 mg, 1.29 mmol). Methanol (10 mL) and N,N-dimethylformamide (2 mL) were added thereto, to which N-Boc-N-methyl-2-aminoacetaldehyde (268 mg, 1.55 mmol) and sodium cyanoborohydride (81 mg, 1.29 mmol) were added, followed by stirring at room temperature for 16 hours. Saturated ammonium chloride solution (3 mL) was added thereto, and then the solvent was concentrated under reduced pressure. Saturated ammonium chloride solution (30 mL) was added thereto again, followed by extraction with ethyl acetate (30 mL×2). The collected organic layer was dried over anhydrous sodium sulfate, filtered, concentrated under reduced pressure and then proceeded to column chromatography (n-hexane/ethyl acetate, 1/2→1/4) to give the titled compound 14b as a white solid (544 mg, 1.07 mmol, 83%).

$^1$H NMR (600 MHz, CDCl$_3$) δ=7.31 (d, J=4 Hz, 1H), 7.24 (d, J=9 Hz, 2H), 6.89 (d, J=4 Hz, 2H), 6.65 (br, 1H), 6.59 (d, J=9 Hz, 1H), 4.85-4.79 (m, 1H), 4.04 (t, J=9 Hz, 1H), 3.90 (ddd, J=16.6, 7, 3 Hz, 1H), 3.79 (dd, J=9, 6 Hz, 1H), 3.74-3.67 (m, 1H), 3.54-3.39 (m, 2H), 3.26 (t, J=6 Hz, 2H), 2.88 (s, 3H), 1.46 (s, 9H)

<4-2> Preparation of Compound 15b

Compound 14b (405 mg, 0.80 mmol) was dissolved in acetic acid (3 mL), to which sodium nitrate (NaNO$_2$) (66 mg, 0.96 mmol) dissolved in distilled water (0.5 mL) was slowly loaded at 0° C., followed by stirring for 30 minutes. Then, zinc (130 mg, 1.99 mmol) was loaded thereto, followed by stirring at 0° C. for 3 hours. Saturated sodium carbonate solution (30 mL) was slowly added thereto, followed by extraction with ethyl acetate (30 mL×2). The collected organic layer was dried over anhydrous sodium sulfate, filtered, concentrated under reduced pressure and then proceeded to column chromatography (n-hexane/ethyl acetate, 1/2→1/4) to give the titled compound 15b as a light brown solid (81 mg, 0.15 mmol, 19%).

Manufacturing Example 5

Preparation of Compound 26

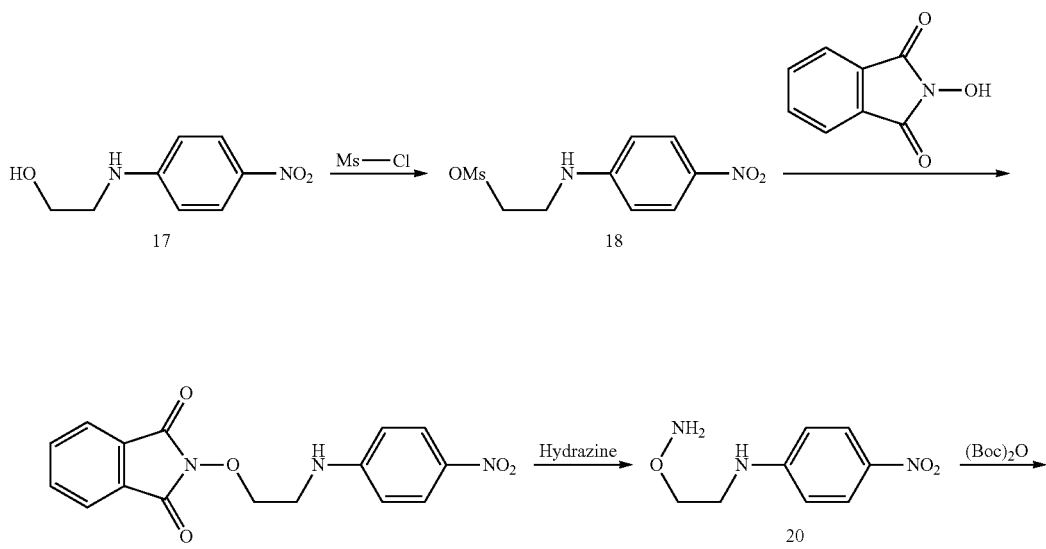

35                                                                                      36
-continued
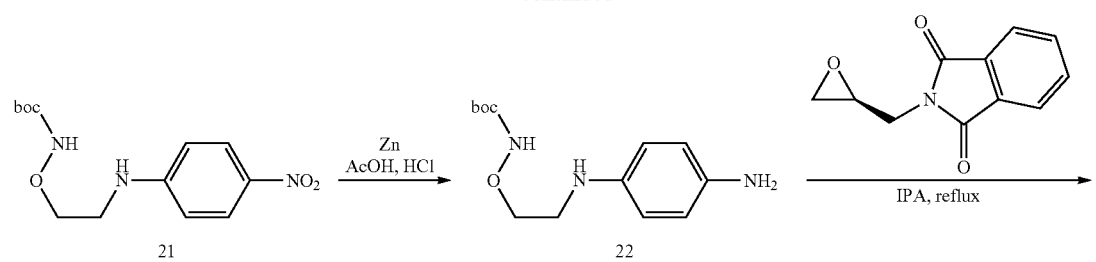
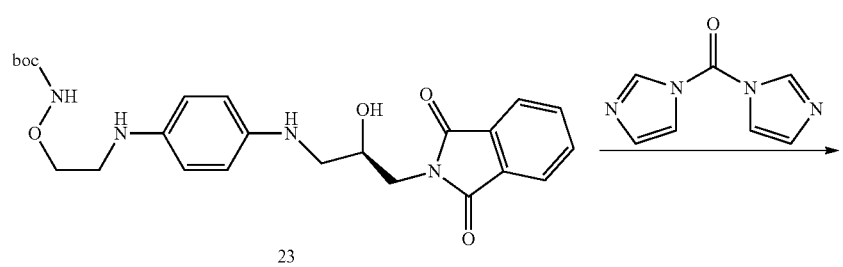
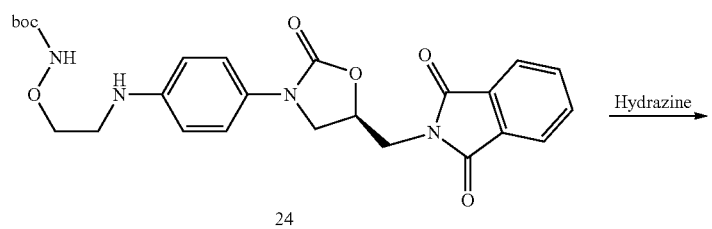
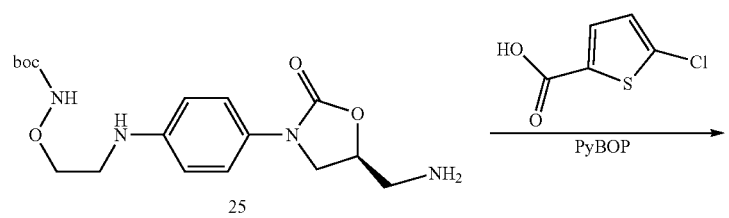
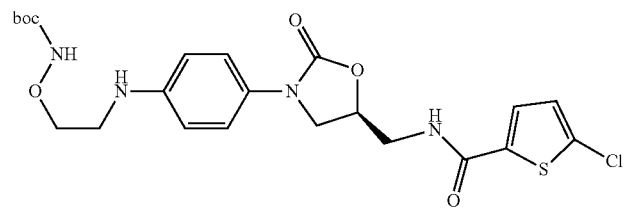

<5-1> Preparation of Compound 18

4-fluoronitrobenzene (5.2 g, 37 mmol) was dissolved in acetonitrile (40 mL), to which 2-aminoethanol (5.2 g, 85 mmol) was added, followed by reflux with stirring for overnight. The reaction solution was cooled down at room temperature, concentrated under reduced pressure, dissolved in ethyl acetate, washed with water, 1N HCl and salt water stepwise. The reactant was dried over anhydrous sodium sulfate, filtered and distillated under reduced pressure to give compound 17. Compound 17 (15 g, 82.33 mmol) and diisopropylethylamine (27 mL, 164 mmol) were dissolved in dichloromethane (150 mL), to which methanesulfonylchloride (9.5 mL) was slowly loaded at 0° C., followed by stirring at room temperature for 2 hours. Upon completion of the reaction, dichloromethane (800 mL) was added to the reaction solution. The reactant was washed with sodium bicarbonate solution (500 mL) and concentrated under reduced pressure to give yellow solid compound 18 (22 g, 82.00 mmol, 99%).

$^1$H NMR (400 MHz, chloroform-$d_1$) δ 8.12 (d, J=9.2 Hz, 2H), 6.60 (d, J=9.2 Hz, 2H), 4.45 (t, J=5.6 Hz, 2H), 3.63 (t, J=5.6 Hz, 2H), 3.06 (s, 3H); LCMS: 183 (M+H$^+$) to $C_8H_{10}N_2O_3S$ <5-2> Preparation of Compound 19

Compound 18 (22 g, 82.00 mmol), hydroxyphthalimide (17.4 g, 107.04 mmol) and triethylamine (17.3 mL, 123.5 mmol) were added to acetonitrile (300 mL), followed by reflux with stirring for 6 hours. Upon completion of the reaction, dichloromethane (1000 mL) was added to the reaction solution. The reactant was washed with 0.5N—HCl solution (500 mL) and saturated sodium bicarbonate solution (500 mL), and concentrated under reduced pressure to give yellow solid compound 19 (26 g, 79.44 mmol, 97%).

$^1$H NMR (400 MHz, chloroform-$d_1$) δ 8.12 (d, J=9.2 Hz, 2H), 7.88 (m, 2H), 7.87 (m, 2H), 6.65 (d, J=9.2 Hz, 2H), 5.83 (br s, 1H), 4.45 (t, J=4.8 Hz, 2H), 3.56 (m, 2H); LCMS: 328 (M+H$^+$) to $C_{16}H_{13}N_3O_5$ <5-3> Preparation of Compound 20

Compound 19 (79.44 mmol) and hydrazine (20 mL) were added to ethanol, followed by reflux with stirring for 2 hours. The reactant was cooled down at room temperature, filtered, and concentrated under reduced pressure to give compound 20 (19 g, crude). This compound was not purified and used for the next reaction.

$^1$H NMR (400 MHz, DMSO-$d_6$) δ 7.94 (d, J=9.6 Hz, 2H), 7.34 (t, J=5.6 Hz, 1H), 6.69 (d, J=9.5 Hz, 2H), 3.68 (t, J=5.2 Hz, 2H), 3.37 (m, 2H); LCMS: 198 (M+H$^+$) to $C_8H_{11}N_3O_3$

<5-4> Preparation of Compound 21

Compound 20 (19 g) and sodium carbonate (21 g, 198 mmol) were dissolved in dioxane (200 mL) and distilled water (200 mL), to which ditertbutoxycarbonyl (26 g, 119 mmol) was slowly added, followed by stirring at room temperature for 4 hours. Upon completion of the reaction, reactant was filtered under reduced pressure, washed with distilled water (1000 mL) and dried to give yellow solid compound 21 (26 g, crude).

$^1$H NMR (400 MHz, chloroform-$d_1$) δ 8.10 (d, J=9.2 Hz, 2H), 6.54 (d, J=9.2 Hz, 2H), 5.50 (s, 1H), 5.04 (s, 1H), 3.91 (t, J=5.2 Hz, 2H), 3.45 (m, 2H), 1.43 (s, 9H); LCMS: 298 (M+H$^+$) to $C_{13}H_{19}N_3O_5$ <5-5> Preparation of Compound 22

Compound 21 (13 g, 40 mmol), acetic acid (132 mL) and concentrated HCl (10 mL, 300 mmol) were dissolved in tetrahydrofurane (200 mL), to which zinc (26 g, 400 mmol) was added at 0° C., followed by stirring for 2 hours. 20% ammonia solution (200 mL) was slowly added at 0° C. and then dimethylenechloride (500 mL) was added thereto. Organic layer was separated, followed by concentration under reduced pressure to give white solid compound 22 (6.5 g, 24.31 mmol, 61%).

$^1$H NMR (400 MHz, chloroform-$d_1$) δ 7.17 (s, 1H), 6.60 (d, J=8.4 Hz, 2H), 6.60 (d, J=8.4 Hz, 2H), 4.03 (t, J=4.8 Hz, 2H), 3.30 (t, J=4.8 Hz, 2H), 1.47 (s, 9H); LCMS: 268 (M+H$^+$) to $C_{13}H_{21}N_3O_3$ <5-6> Preparation of Compound 23

Compound 22 (6.5 g, 24.31 mmol) and (S)-glycidylphthalimide (3.95 g, 19.45 mmol) were added to isopropyl alcohol (100 mL), followed by reflux with stirring for 6 hours. Upon completion of the reaction, the reactant was concentrated under reduced pressure, followed by column chromatography to give white solid compound 23 (9 g, crude).

$^1$H NMR (400 MHz, chloroform-$d_1$) δ 7.85 (m, 2H), 7.79 (m, 2H), 6.33 (d, J=9.2 Hz, 2H), 6.21 (d, J=9.2 Hz, 2H), 4.07 (m, 3H), 3.58-3.31 (m, 6H), 1.46 (s, 9H); LCMS: 471 (M+H$^+$) to $C_{24}H_{30}N_4O_6$ <5-7> Preparation of Compound 24

Compound 23 (9 g, crude) and carbodiimidazole (3.5 g, 29.16 mmol) were added to tetrahydrofurane (150 mL), followed by stirring for 12 hours. Upon completion of the reaction, the reactant was concentrated under reduced pressure, followed by column chromatography to give white solid compound 24 (1.6 g, 3.22 mmol).

$^1$H NMR (400 MHz, chloroform-$d_1$) δ 7.88 (m, 2H), 7.75 (m, 2H), 7.28 (d, J=8.8 Hz, 2H), 6.55 (d, J=8.8 Hz, 2H), 4.95 (m, 1H), 4.17-3.82 (m, 6H), 3.37 (t, J=5.2 Hz, 2H), 1.46 (s, 9H); LCMS: 497 (M+H$^+$) to $C_{25}H_{28}N_4O_7$ <5-8> Preparation of Compound 25

Compound 24 (1.6 g, 3.22 mmol) and hydrazine (1.6 mL, 32.20 mmol) were added to ethyl alcohol (30 mL), followed by reflux with stirring for 2 hours. The reactant was cool down at room temperature, filtered and concentrated under reduced pressure to give compound 25 (1.3 g, crude). This compound was not purified and used for the next reaction.

$^1$H NMR (400 MHz, chloroform-$d_1$) δ 7.33 (d, J=9.2 Hz, 2H), 6.66 (d, J=9.2 Hz, 2H), 4.63 (m, 1H), 4.03 (m, 3H), 3.77 (dd, J=6.4 2.0 Hz, 1H), 3.34 (t, J=5.2 Hz, 2H), 3.03 (m, 2H), 1.49 (s, 9H); LCMS: 367 (M+H$^+$) to $C_{17}H_{26}N_4O_5$ <5-9> Preparation of Compound 26

Compound 25 (1.3 g, 3.22 mmol), 5-chlorothiophene-2-carboxylic acid (0.68 g, 4.19 mmol) and PyBOP [(Benzotriazol-1-yloxy)tripyrrolidinophosphonium hexafluorophosphate] (2.5 g, 4.83 mmol) were added to N,N-dimethylformamide (20 mL), to which diisopropylethylamine (1.06 mL, 6.44 mmol) was slowly added at 0° C., followed by stirring for 1 hour. Upon completion of the reaction, ethylacetate (300 mL) was added to the reaction solution. The reactant was washed with distilled water (200 mL) twice, and concentrated under reduced pressure to give white solid compound 26 (1.6 g, 3.13 mmol).

$^1$H NMR (400 MHz, DMSO-$d_6$) δ 10.05 (s, 1H), 8.97 (t, J=5.6 Hz, 1H), 7.70 (d, J=4.0 Hz, 1H), 7.20 (m, 3H), 6.60 (d, J=8.4 Hz, 2H), 4.76 (m, 1H), 4.07 (t, J=8.8 Hz, 1H), 3.83 (t, J=5.6 Hz, 2H), 3.74 (m, 1H), 3.57 (t, J=5.2 Hz, 2H), 3.21 (t, J=5.6 Hz, 2H), 1.40 (s, 9H); LCMS: 511 (M+H$^+$) to $C_{22}H_{27}ClN_4O_6S$

Example 1

Preparation of Compound 100

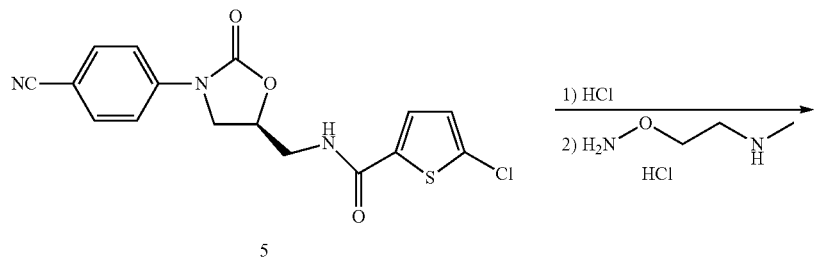

Compound 5 (5.0 g, 13.8 mmol) obtained in Manufacturing Example 1 was added to anhydrous methanol (200 mL), followed by bubbling HCl gas at 0° C. for 30 minutes. Methanol (100 mL) was added thereto, followed by bubbling HCl gas again for 30 more minutes, followed by stirring at room temperature for 2 hours. The reactant was concentrated under reduced pressure to eliminate remaining HCl. Acetic acid (120 mL) and 2-(N-methylamino)ethyl-hydroxylamine hydrochloride (3.5 g, 27.6 mmol) were added thereto, followed by reflux for overnight. The reaction solution was concentrated under reduced pressure, dissolved in ethyl acetate, and washed with saturated NaHCO$_3$ solution, followed by separation using column chromatography to give the titled compound 100 as a white solid (1.85 g, 4.3 mmol, 31%).

$^1$H NMR (400 MHz, CDCl$_3$) δ 7.54 (d, J=9.0 Hz, 2H), 7.44 (d, J=9.0 Hz, 2H), 7.34 (d, J=4.2 Hz, 1H), 6.89 (brt, 1H), 4.80 (m, 1H), 4.12 (t, J=4.8 Hz, 2H), 4.04 (t, J=9.0 Hz, 1H), 3.85-3.80 (m, 2H), 3.69-3.64 (m, 1H), 3.45 (t, J=4.8 Hz, 2H), 2.76 (s, 3H); LCMS: 435 (M+H$^+$) to C$_{19}$H$_{19}$ClN$_4$O$_4$S

Example 2

Preparation of Compound 101

Compound 101 was prepared as a white solid (17 mg, 0.04 mmol, 14%) by the same manner as described in Example 1 by using compound 5 (0.1 g, 0.27 mmol) obtained in Manufacturing Example 1 and (aminoethyl)hydroxylamine (62 mg, 0.8 mmol).

$^1$H NMR (400 MHz, DMSO-d$_6$) δ 8.98 (t, J=6.0 Hz, 1H), 7.68 (d, J=4.0 Hz, 1H), 7.63 (d, J=8.8 Hz, 2H), 7.57 (d, J=8.8 Hz, 2H), 7.19 (d, J=4.0 Hz, 1H), 7.07 (s, 1H), 4.85 (m, 1H), 4.19 (t, J=8.8 Hz, 1H), 3.86-3.81 (m, 3H), 3.61 (t, J=5.2 Hz, 2H), 3.38 (m, 2H); LCMS: 421 (M+H$^+$) to C$_{18}$H$_{17}$ClN$_4$O$_4$S

Example 3

Preparation of Compound 102

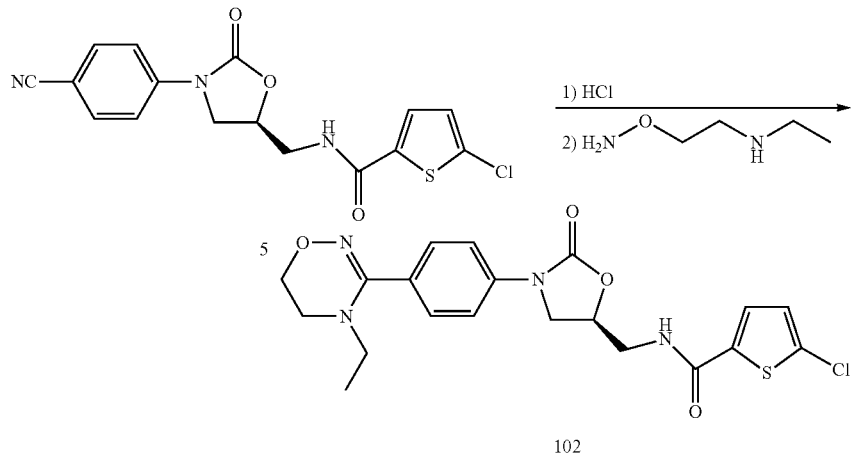

Compound 102 was prepared as a white solid (30 mg, 48%) by the same manner as described in Example 1 by using compound 5 (100 mg, 0.27 mmol) obtained in Manufacturing Example 1 and O-[2-(2-ethylamino)-ethyl]-hydroxylamine (15 mg, 0.139 mmol).

$^1$H NMR (400 MHz, CDCl$_3$) δ 7.52 (d, J=8.4 Hz, 2H), 7.42 (d, J=8.4 Hz, 2H), 7.37 (d, J=3.6 Hz, 1H), 7.28-7.22 (m, 1H), 6.85 (d, J=3.6 Hz, 1H), 4.82-4.71 (m, 1H), 4.11 (t, J=4.4 Hz, 2H), 3.98 (t, J=8.8 Hz, 1H), 3.83-3.72 (m, 2H), 3.66-3.56 (m, 1H), 3.43 (t, J=4.4 Hz, 2H), 3.01 (q, J=7.2 Hz, 2H), 1.03 (t, J=4.4 Hz, 3H); LCMS: 449 (M+H$^+$) to C$_{20}$H$_{21}$ClN$_4$O$_4$S

Example 4

Preparation of Compound 103

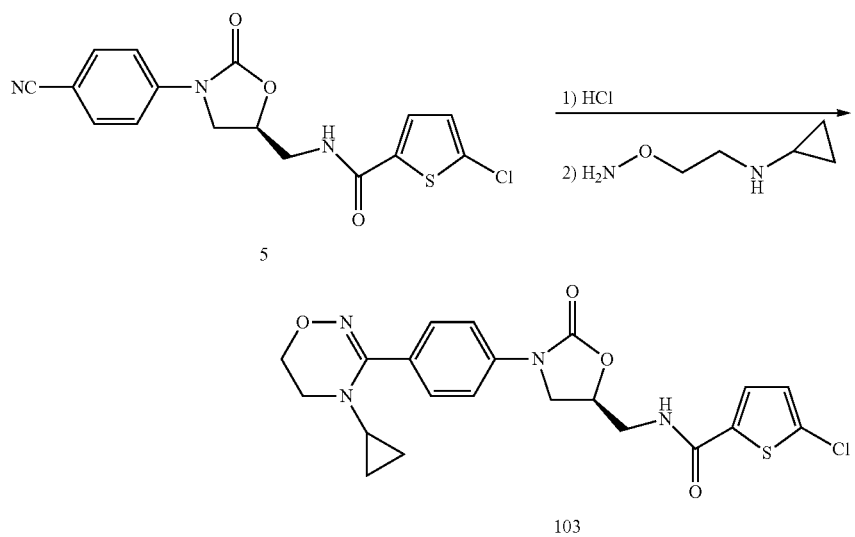

Compound 103 was prepared as a white solid (31 mg, 29%) by the same manner as described in Example 1 by using compound 5 (100 mg, 0.27 mmol) obtained in Manufacturing Example 1 and O-[2-(2-cyclopropylamino)-ethyl]-hydroxylamine (27 mg, 0.23 mmol).

$^1$H NMR (400 MHz, CDCl$_3$) δ 7.52 (d, J=7.6 Hz, 2H), 7.46 (d, J=7.6 Hz, 2H), 7.38 (d, J=3.6 Hz, 1H), 7.23-7.18 (m, 1H), 6.87 (d, J=3.6 Hz, 1H), 4.85-4.72 (m, 1H), 4.06 (t, J=4.4 Hz, 2H), 4.02 (t, J=8.4 Hz, 1H), 3.85-3.74 (m, 2H), 3.68-3.55 (m, 1H), 3.53 (t, J=4.4 Hz, 2H), 2.62-2.51 (m, 1H), 0.51-0.32 (m, 4H); LCMS: 461 (M+H$^+$) to C$_{21}$H$_{21}$ClN$_4$O$_4$S

Example 5

Preparation of Compound 104

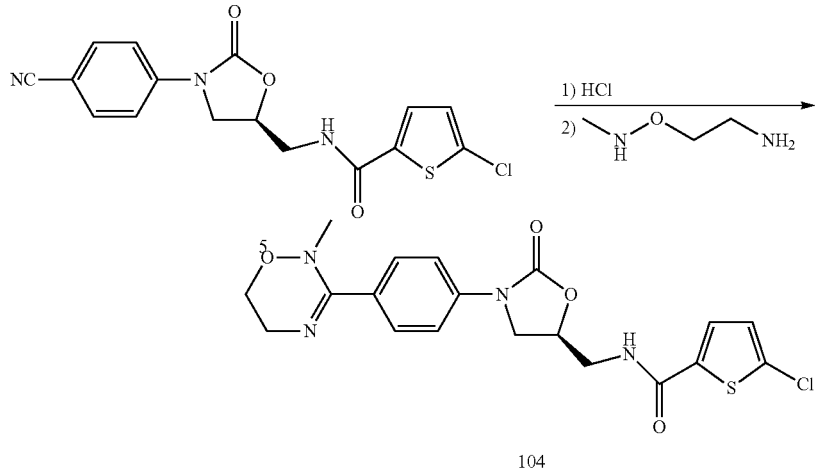

Compound 104 was prepared as a white solid (63.7 mg, 0.146 mmol, 58%) by the same manner as described in Example 1 by using compound 5 (100 mg, 0.27 mmol) obtained in Manufacturing Example 1 and N-methyl-O-(2-aminoethyl)hydroxylamine dihydrochloride (180.0 mg, 1.104 mmol).

$^1$H NMR (400 MHz, DMSO-d$_6$) δ 9.07 (t, J=6.4 Hz, 1H), 7.70 (d, J=4.4 Hz, 1H), 7.54 (m, 4H), 7.14 (d, J=4.4 Hz, 1H), 4.80 (m, 1H), 4.15 (t, J=8.8 Hz, 1H), 3.86 (dd, J=8.8 Hz, 8.8 Hz, 1H), 3.81 (t, J=4.8 Hz, 2H), 3.55-3.48 (m, 4H), 2.82 (s, 3H); LCMS: 435 (M+H$^+$) to C$_{19}$H$_{19}$ClN$_4$O$_4$S

Example 6

Preparation of Compound 105

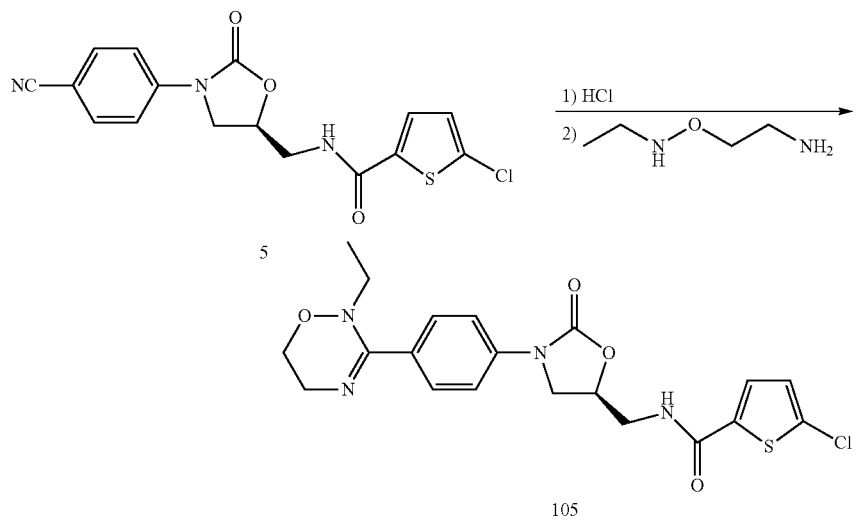

Compound 105 was prepared as a light yellow solid (9.1 mg, 0.020 mmol, 9%) by the same manner as described in Example 1 by using compound 5 (80.0 g, 0.221 mmol) obtained in Manufacturing Example 1 and N-ethyl-O (2-aminoethyl)hydroxylamine dihydrochloride (300.0 mg, 1.69 mmol).

$^1$H NMR (600 MHz, DMSO-d$_6$) δ 9.37 (br, 1H), 7.88 (m, 1H), 7.79 (d, J=6.0 Hz, 2H), 7.73 (d, J=5.6 Hz, 2H), 7.20 (d, J=4.2 Hz, 1H), 4.91 (m, 1H), 4.24 (t, J=8.7 Hz, 1H), 4.05 (dd, J=8.7 Hz, 8.7 Hz, 1H), 3.66 (t, J=4.8 Hz, 2H), 3.63-3.54 (m, 4H), 2.81 (q, J=7.2 Hz, 2H), 1.24 (t, J=7.2 Hz, 3H); LCMS: 449 (M+H$^+$) to $C_{20}H_{21}ClN_4O_4S$

Example 7

Preparation of Compound 106

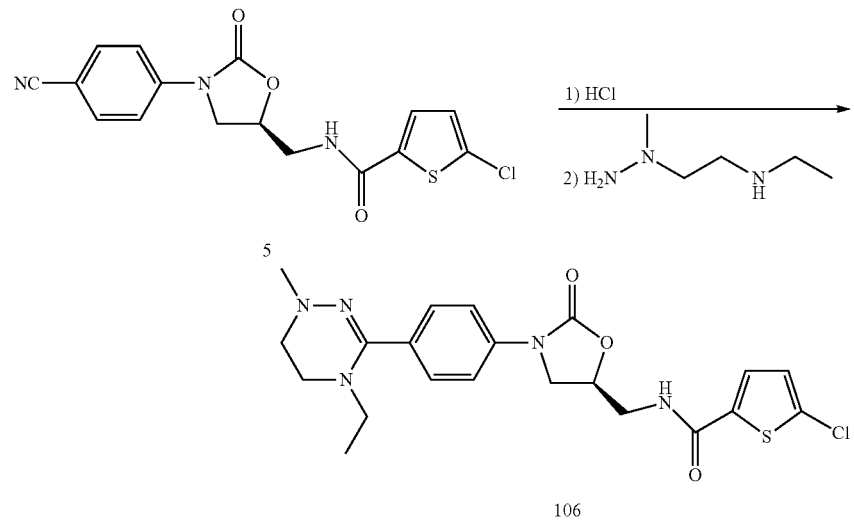

Compound 106 was prepared as a white solid (20 mg, 0.04 mmol, 16%) by the same manner as described in Example 1 by using compound 5 (100 mg, 0.27 mmol) obtained in Manufacturing Example 1 and 2-(1-methylhydrazinyl)-N-ethylethaneamine (93 mg, 0.8 mmol).

$^1$H NMR (600 MHz, DMSO-d$_6$) δ 8.99 (t, J=5.4 Hz, 1H), 7.69 (d, J=3.6 Hz, 1H), 7.53 (d, J=8.4 Hz, 2H), 7.36 (t, J=8.4 Hz, 2H), 7.19 (d, J=3.6 Hz, 1H), 4.84 (m, 1H), 4.19 (t, J=9.6 Hz, 1H), 3.86 (dd, J=8.4 6.6 Hz, 1H), 3.61 (t, J=5.4 Hz, 2H), 3.31 (m, 2H), 2.92 (m, 2H), 2.80 (br s, 2H), 2.59 (s, 3H), 0.94 (t, J=7.2 Hz, 1H) (2 equivalent acetic acid by NMR); LCMS: 462 (M+H$^+$) to $C_{21}H_{24}ClN_5O_3S$ Example 8

Preparation of Compound 107

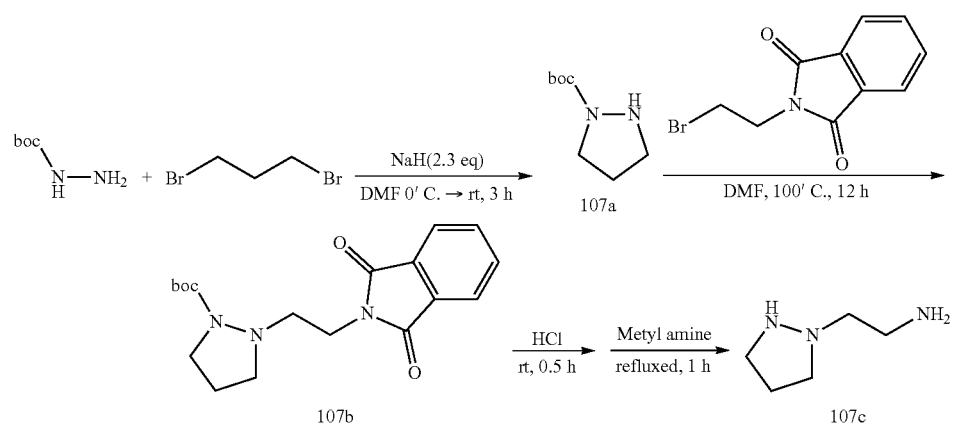

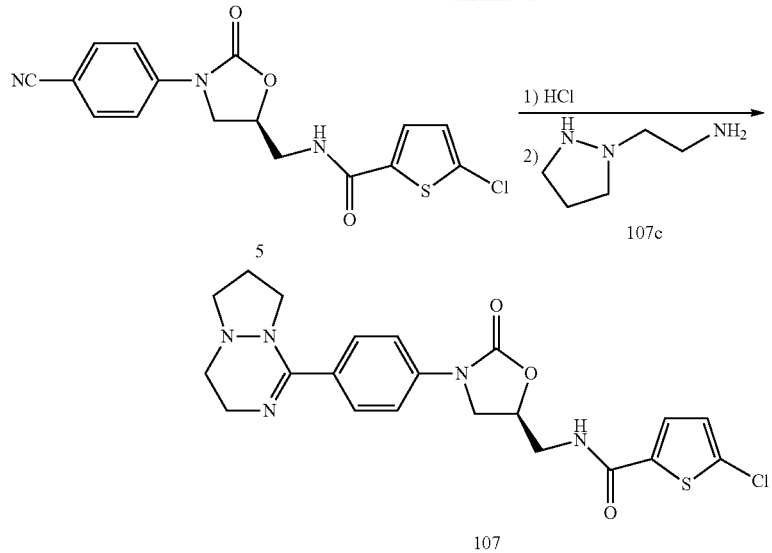

NaH (3.3 g, 87.01 mmol) was added to N,N-dimethylformamide (30 mL), followed by stirring for 15 minutes. Tert-butylchabazite (5 g, 37.83 mmol) was dissolved in N,N-dimethylformamide (10 mL), which was slowly added thereto at 0° C. Dibromopropane (7.6 g, 37.83 mmol) was also added thereto at 0° C., followed by stirring at room temperature for 3 hours. The reactant was cooled down at 0° C. and washed with distilled water (50 mL). Upon completion of the reaction, the reactant was dissolved in ethyl acetate (500 mL), followed by washing with sodium bicarbonate solution (50 mL) three times. Column chromatography was performed to give oil type compound 107a (2.4 g, 13.93 mmol, 36.7%).

$^1$H NMR (400 MHz, chloroform-d$_1$) δ 3.85 (s, 1H), 3.45 (t, J=7.2 Hz, 2H), 3.04 (t, J =6.4 Hz, 2H), 2.03 (m, 2H), 1.49 (s, 9H); LCMS: 173 (M+H$^+$) to C$_8$H$_{16}$N$_2$O$_2$ Compound 107a (1.5 g, 8.71 mmol), N-2-bromophthalimide (2.33 g, 8.71 mmol) and potassium carbonate (1.32 g, 9.58 mmol) were added to N,N-dimethylformamide (10 mL), followed by stirring at 100° C. for 12 hours. The reactant was dissolved in ethyl acetate (200 mL), followed by washing with sodium bicarbonate solution (30 mL) three times. Column chromatography was performed to give oil type compound 107b (1.7 g, 4.92 mmol, 56.2%).

$^1$H NMR (400 MHz, chloroform-d$_1$) δ 7.89 (m, 2H), 7.74 (m, 2H), 3.94 (t J=4.4 Hz, 2H), 3.90 (t, J=5.2 Hz, 2H), 3.11 (t, J=6.0 Hz, 2H), 3.06 (t, J=4.4 Hz, 2H), 2.01 (m, 2H), 1.48 (s, 9H); LCMS: 346 (M+H$^+$) to C$_{18}$H$_{23}$N$_3$O$_4$ Compound 107b (0.5 g, 1.45 mmol) was added to 4M–HCl (in dioxane) (5 mL), followed by stirring for 0.5 hour. The reaction mixture was concentrated under reduced pressure, to which methyl alcohol (5 mL) and methyl amine (4 mL) were added, followed by reflux with stirring for 1 hour. The reactant was concentrated under reduced pressure to give compound 107c, which was not purified any more and used for the next reaction.

LCMS: 116 (M+H$^+$) to C$_5$H$_{13}$N$_3$

Compound 5 (100 mg, 0.27 mmol) obtained in Manufacturing Example 1 was added to anhydrous methyl alcohol (10 mL), followed by bubbling HCl gas at 0° C. for 30 minutes and stirring at room temperature for 2 hours. The reactant was concentrated under reduced pressure to eliminate remaining HCl. Anhydrous methyl alcohol (10 mL) and compound 107c (300 mg, 0.8 mmol) were added thereto stepwise, followed by stirring at room temperature for 12 hours and concentration under reduced pressure. Then, prep TLC was performed to give the title compound 107 as a white solid (60 mg, 0.13 mmol, 48%).

$^1$H NMR (400 MHz, DMSO-d$_6$) δ 9.12 (t J=5.6 Hz, 1H), 7.77-7.64 (m, 5H), 7.14 (d, J=4.4 Hz, 1H), 4.84 (m, 1H), 4.18 (t, J=8.8 Hz, 1H), 3.90 (dd J=8.8, 6.0 Hz, 1H), 3.70 (t, J=6.8 Hz, 1H), 3.65 (t, J=6.8 Hz, 1H), 3.59-3.52 (m, 3H), 3.25 (m, 1H), 3.11 (m, 1H), 2.95 (m, 1H), 2.65 (m, 1H), 2.55 (m, 1H), 2.08 (m, 2H); LCMS: 460 (M+H$^+$) to C$_{21}$H$_{22}$ClN$_5$O$_3$S

Example 9

Preparation of Compound 108

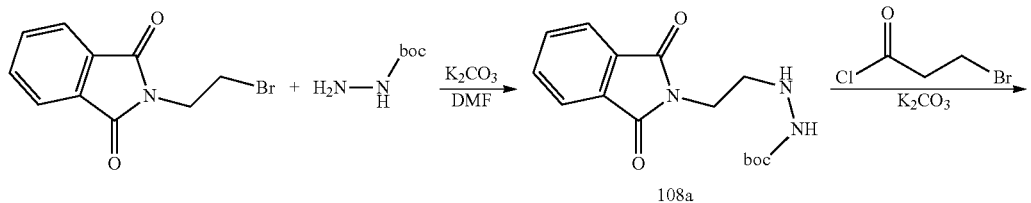

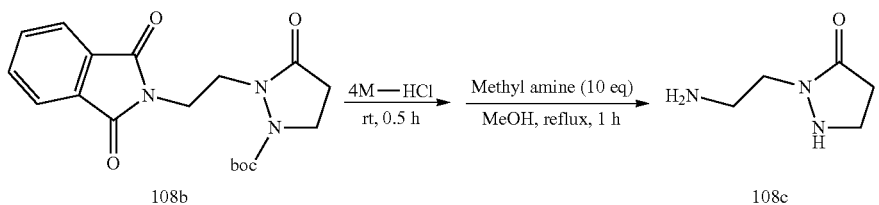

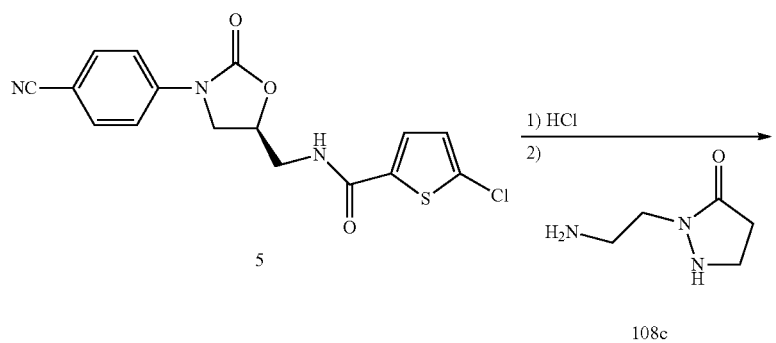

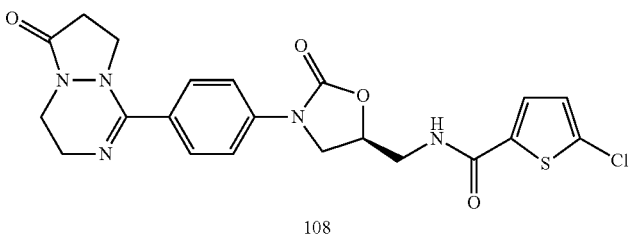

Tertbutylchabazite (t-butyl carbazate) (2.5 g, 18.91 mmol), N (bromoethyl)phthalimide (5.25 g, 20.80 mmol) and potassium carbonate (3.14 g, 22.70 mmol) were added to N,N-dimethylformamide (30 mL), followed by stirring at 90° C. for 12 hours. Upon completion of the reaction, the reactant was dissolved in ethyl acetate (250 mL), followed by washing with sodium bicarbonate solution (150 mL) three times. After concentration under reduced pressure, column chromatography was performed to give white solid compound 108a (1 g, 3.2 mmol, 19%).

$^1$H NMR (400 MHz, chloroform-$d_1$) δ 7.85 (m, 2H), 7.73 (m, 2H), 6.49 (s, 1H), 4.12 (s, 1H), 3.83 (t, J=3.6 Hz, 2H), 3.05 (m, 2H), 1.46 (s, 9H); LCMS: 306 (M+H$^+$) to $C_{15}H_{19}N_3O_4$ Compound 108a (0.9 g, 2.95 mmol) and potassium carbonate (1.03 g, 7.4 mmol) were dissolved in N,N-dimethylformamide (10 mL), to which 3-bromopropanoyl chloride (0.7 g, 3.6 mmol) was added, followed by stirring at 90° C. for 5 hours. Ethyl acetate (100 mL) was added thereto, followed by washing with sodium bicarbonate solution (30 mL). After concentration under reduced pressure, column chromatography was performed to give oil type compound 108b (230 mg, 0.64 mmol, 22%).

$^1$H NMR (400 MHz, chloroform-$d_1$) δ 7.85 (m, 2H), 7.73 (m, 2H), 6.49 (s, 1H), 4.12 (s, 1H), 3.83 (t, J=3.6 Hz, 2H), 3.05 (m, 2H), 1.46 (s, 9H); LCMS: 360 (M+H$^+$) to $C_{18}H_{21}N_3O_5$ Compound 108b (230 mg, 0.64 mmol) was added to 4M-HCl (in dioxane) (2 mL), followed by stirring for 1 hour. The reactant was concentrated under reduced pressure, to which methyl alcohol (5 mL) and methyl amine (2 mL) were added, followed by stirring for 1 hour. The reactant was concentrated under reduced pressure to give compound 108c (103 mg, 0.64 mmol), which was not purified any more and used for the next reaction.

LCMS: 130 (M+H$^+$) to $C_5H_{11}N_3O$

Compound 108 was prepared as a white solid (26 mg, 0.05 mmol, 19%) by the same manner as described in Example 1 by using compound 5 (0.1 g, 0.27 mmol) obtained in Manufacturing Example 1 and compound 108c (103 mg, 0.64 mmol).

$^1$H NMR (600 MHz, DMSO-$d_6$) δ 9.09 (t, J=4.8 Hz, 1H), 7.79 (d, J=8.4 Hz, 2H), 7.72-7.71 (m, 3H), 7.19 (d, J=4.2 Hz, 1H), 4.89 (m, 1H), 4.24 (t, J=9.0 Hz, 1H), 4.12 (t, J=7.8 Hz, 2H), 3.94-3.89 (m, 3H), 3.62 (m, 2H), 3.53 (t, J=4.8 Hz, 2H), 2.80 (t, J=8.4 Hz, 2H), 3.59-3.52 (m, 3H), 3.25 (m, 1H), 3.11 (m, 1H), 2.95 (m, 1H), 2.65 (m, 1H), 2.55 (m, 1H), 2.08 (m, 2H); LCMS: 474 (M+H$^+$) to $C_{21}H_{20}ClN_5O_4S$

Example 10

Preparation of Compound 109

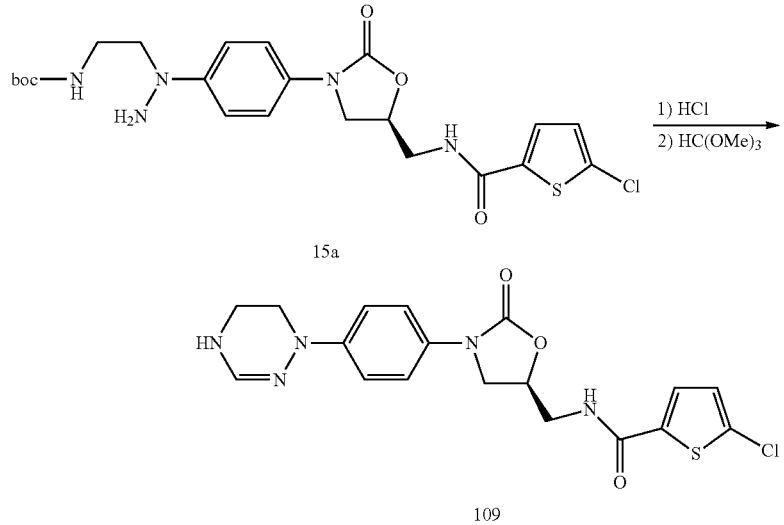

Compound 15a (450 mg, 0.88 mmol) obtained in Manufacturing Example 3 was dissolved in dichloromethane (10 mL), to which HCl (4 M 1,4-dioxane solution) (10 mL) was added, followed by stirring at room temperature for 1 hour. The reactant was concentrated under reduced pressure and dried to give light yellow solid compound (425 mg, 0.88 mmol, 100%). This compound (392 mg, 0.81 mmol) was dissolved in acetic acid (4 mL), to which trimethylorthoformate (2 mL) was added, followed by reflux with stirring. 10 hours later, after solvent was evaporated all, column chromatography (dichloromethane/methanol (v/v) 20/1→12/1) was performed to give the title compound 109 as a light yellow solid (215 mg, 5.12 mmol, 63%).

$^1$H NMR (400 MHz, CDCl$_3$) δ 7.35 (d, J=9.2 Hz, 2H), 7.33 (d, J=4.4 Hz, 1H), 7.14 (d, J=9.2 Hz, 2H), 7.01 (t, J=6.4 Hz, 1H), 6.88 (s, 1H), 6.85 (d, J=4.4 Hz, 1H), 4.87-4.79 (m, 1H), 4.06 (t, J=9 Hz, 1H), 3.86 (ddd, J=14.4, 6, 3 Hz, 1H), 3.81 (dd, J=9, 6.4 Hz, 1H), 3.69 (dt, J=14.4, 6 Hz, 1H), 3.62-3.58 (m, 2H), 3.55-3.51 (m, 2H); LCMS: 420 (M+H$^+$) to C$_{18}$H$_{18}$ClN$_5$O$_3$S

Example 11

Preparation of Compound 110

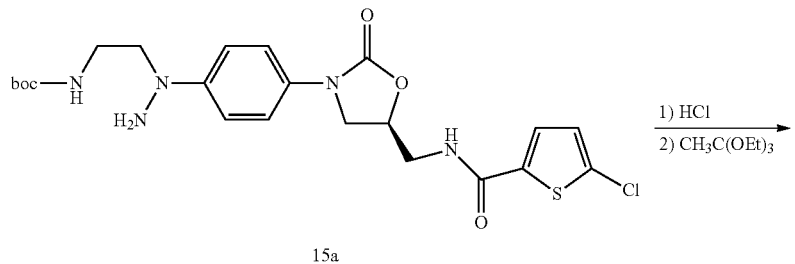

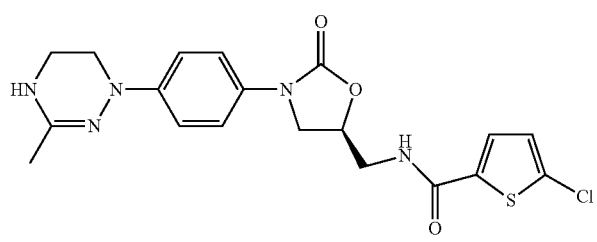

Compound 15a obtained in Manufacturing Example 3 was used to give the title compound 110 by the similar manner as described in Example 10 by using triethylorthoacetate instead of trimethylorthoformate of Example 10.

$^1$H NMR (600 MHz, CDCl$_3$) δ 7.36 (d, J=9 Hz, 2H), 7.30 (d, J=4 Hz, 1H), 7.17 (d, J=9 Hz, 2H), 6.90 (d, J=4.2 Hz, 1H), 6.49 (br t, 1H), 4.85-4.80 (m, 1H), 4.28 (br, 1H), 4.08 (t, J=9 Hz, 1H), 3.95-3.90 (m, 1H), 3.79 (t, J=7.8 Hz, 1H), 3.72-3.67 (m, 1H), 3.62-3.57 (m, 2H), 3.49-3.44 (m, 2H), 1.98 (s, 3H); LCMS: 434 (M+H$^+$) to C$_{19}$H$_{20}$ClN$_5$O$_3$S

Example 12

Preparation of Compound 111

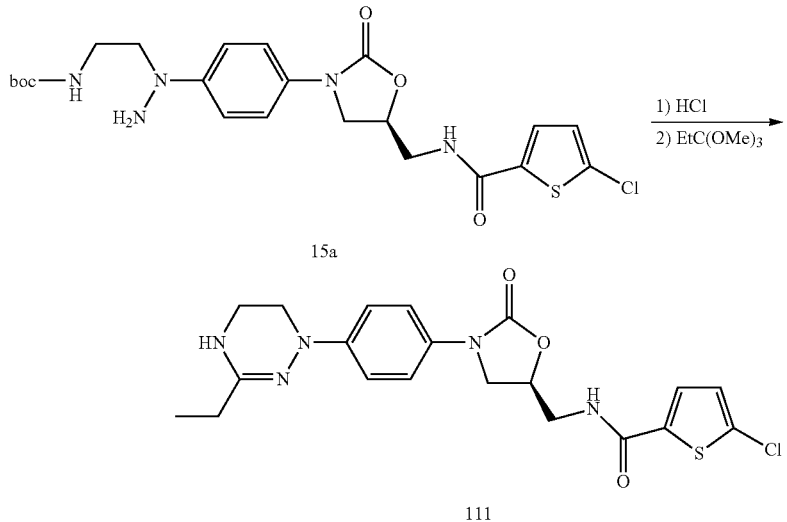

Compound 15a obtained in Manufacturing Example 3 was used to give the title compound III by the similar manner as described in Example 10 by using triethylorthopropionate instead of trimethylorthoformate of Example 10.

$^1$H NMR (600 MHz, CDCl$_3$) δ 7.35 (d, J=9 Hz, 2H), 7.30 (d, J=4.2 Hz, 1H), 7.18 (d, J=9 Hz, 2H), 6.90 (d, J=4.2 Hz, 1H), 6.53 (br t, 1H), 4.85-4.80 (m, 1H), 4.27 (br, 1H), 4.08 (t, J=9 Hz, 1H), 3.92 (ddd, J=14.4, 6.6, 3 Hz, 1H), 3.79 (t, J=7.8 Hz, 1H), 3.72-3.67 (m, 1H), 3.62-3.57 (m, 2H), 3.50-3.44 (m, 2H), 2.26 (q, J=7.8 Hz, 2H), 1.20 (t, J=7.8 Hz, 3H); LCMS: 448 (M+H$^+$) to C$_{20}$H$_{22}$ClN$_5$O$_3$S Example 13

Preparation of Compound 112

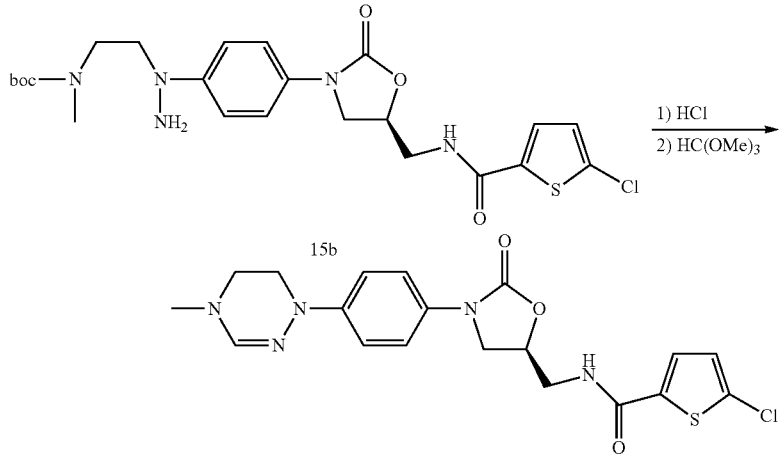

Compound 15b obtained in Manufacturing Example 4 was used to give the title compound 112 by the similar manner as described in Example 10.

$^1$H NMR (600 MHz, CDCl$_3$) δ 7.35 (d, J=9 Hz, 2H), 7.33 (d, J=4.5 Hz, 1H), 7.13 (d, J=9 Hz, 2H), 6.93 (t, J=6 Hz, 1H), 6.85 (d, J=4.5 Hz, 1H), 6.64 (s, 1H), 4.86-4.80 (m, 1H), 4.06 (t, J=9 Hz, 1H), 3.91-3.85 (m, 1H), 3.80 (dd, J=9, 7 Hz, 1H), 3.71-3.65 (m, 1H), 3.54 (t, J=4.8 Hz, 2H), 3.43 (t, J=4.8 Hz, 2H), 2.90 (s, 3H); LCMS: 434 (M+H$^+$) to C$_{19}$H$_{20}$ClN$_5$O$_3$S

Example 14

Preparation of Compound 113

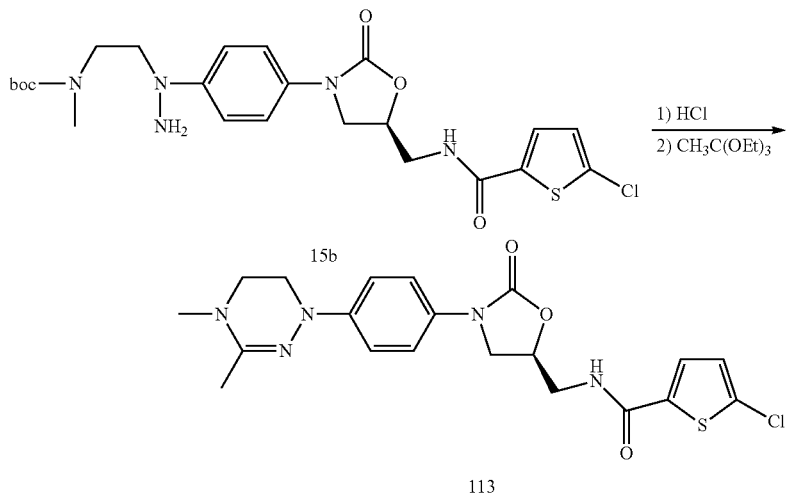

Compound 15b obtained in Manufacturing Example 4 was used to give the title compound 113 by the similar manner as described in Example 10 by using triethylorthoacetate instead of trimethylorthoformate of Example 10.

$^1$H NMR (600 MHz, CDCl$_3$) δ 7.34 (d, J=9 Hz, 2H), 7.31 (d, J=4 Hz, 1H), 7.15 (d, J=9 Hz, 2H), 6.88 (d, J=4 Hz, 1H), 6.69 (t, J=6 Hz, 1H), 4.84-4.78 (m, 1H), 4.06 (t, J=9 Hz, 1H), 3.90 (ddd, J=11, 7, 3 Hz, 1H), 3.79 (dd, J=9, 6.6 Hz, 1H), 3.68 (dt, J=14.4, 6.6 Hz, 1H), 3.52 (t, J=5 Hz, 2H), 3.44 (t, J=5 Hz, 2H), 2.93 (s, 3H), 2.05 (s, 3H); LCMS: 448 (M+H$^+$) to C$_{20}$H$_{22}$ClN$_5$O$_3$S

Example 15

Preparation of Compound 114

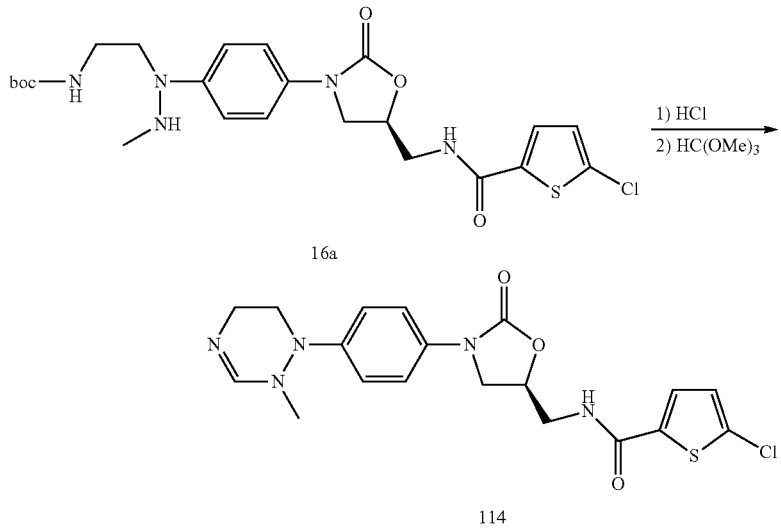

Compound 16a obtained in Manufacturing Example 3 was used to give the title compound 114 as a white solid (7.4 mg, 0.014 mmol, 47%) by the similar manner as described in Example 10.

$^1$H NMR (600 MHz, DMSO-$d_6$) δ 9.03 (t, J=5.4 Hz, 1H), 8.65 (s, 1H), 7.68 (d, J=3.6 Hz, 1H), 7.55 (d, J=8.4 Hz, 2H), 7.19 (d, J=3.6 Hz, 1H), 7.14 (d, J=8.4 Hz, 2H), 4.88-4.81 (m, 1H), 4.17 (t, J=9 Hz, 1H), 3.85-3.81 (m, 1H), 3.70-3.50 (m, 4H), 3.29 (s, 3H), 3.13-3.05 (m, 2H); LCMS: 434 (M+H$^+$) to $C_{19}H_{20}ClN_5O_3S$

Example 16

Preparation of Compound 115

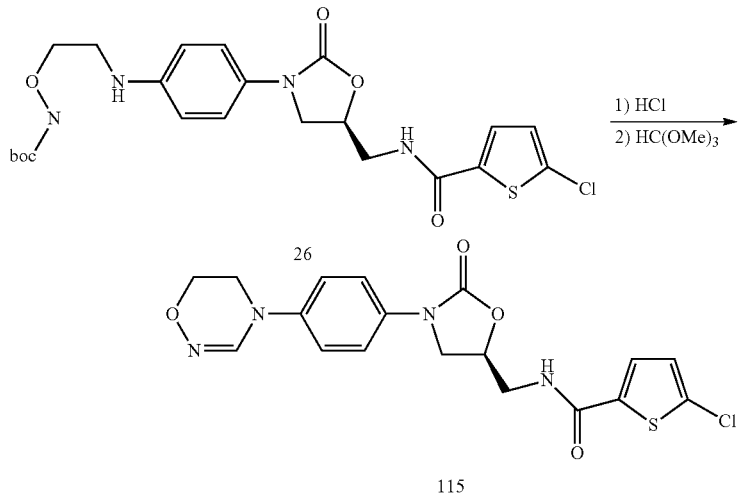

Compound 26 obtained in Manufacturing Example 5 was added to 4 M HCl (2 mL), followed by stirring for one hour. The reactant was concentrated under reduced pressure, to which trimethylorthoformate (2 mL) and acetic acid (4 mL) were added, followed by reflux with stirring for 12 hours. Column chromatography was performed with the reactant to give the title compound 115 as a white solid (11 mg, 0.03 mmol, 8%).

$^1$H NMR (400 MHz, chloroform-$d_1$) δ 7.55 (s, 1H), 7.50 (d, J=9.2 Hz, 2H), 7.42 (br s, 1H), 7.39 (d, J=4.0 Hz, 1H), 7.03 (d, J=9.2 Hz, 2H), 6.89 (d, J=4.0 Hz, 1H), 4.86 (m, 1H), 4.20 (t, J=4.8 Hz, 2H), 4.12 (m, 1H), 3.87 (m, 1H), 3.83-3.74 (m, 4H); LCMS: 421 (M+H$^+$) to $C_{18}H_{17}ClN_4O_4S$ Example 17

Preparation of Compound 116

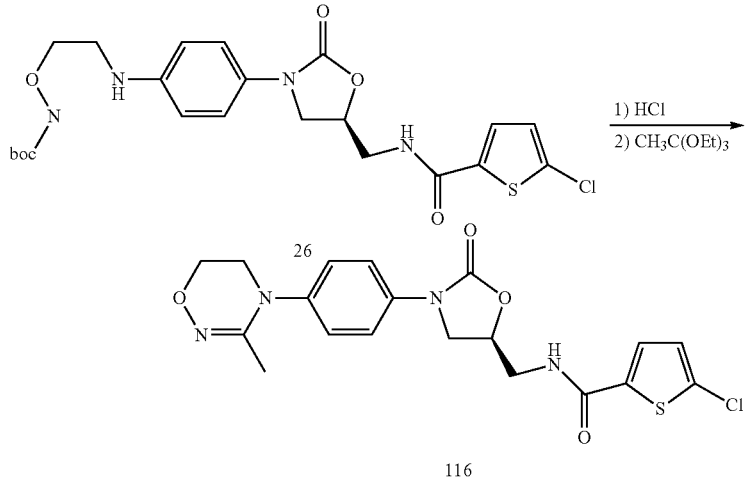

Compound 116 was prepared as a white solid by the similar manner as described in Example 14 by using compound 26 obtained in Manufacturing Example 5.

$^1$H NMR (400 MHz, DMSO-d$_6$) δ 8.93 (t, J=5.6 Hz, 1H), 7.63 (d, J=4.2 Hz, 1H), 7.50 (d, J=8.8 Hz, 2H), 7.25 (d, J=8.8 Hz, 2H), 7.14 (d, J=4.2 Hz, 1H), 4.79 (m, 1H), 4.13 (t, J=8.8 Hz, 1H), 3.94 (t, J=4.6 Hz, 2H), 3.79 3.56-3.51 (m, 4H), 1.56 (s, 3H); LCMS: 435 (M+H$^+$) to C$_{19}$H$_{19}$ClN$_4$O$_4$S

Example 18

Preparation of Compound 117

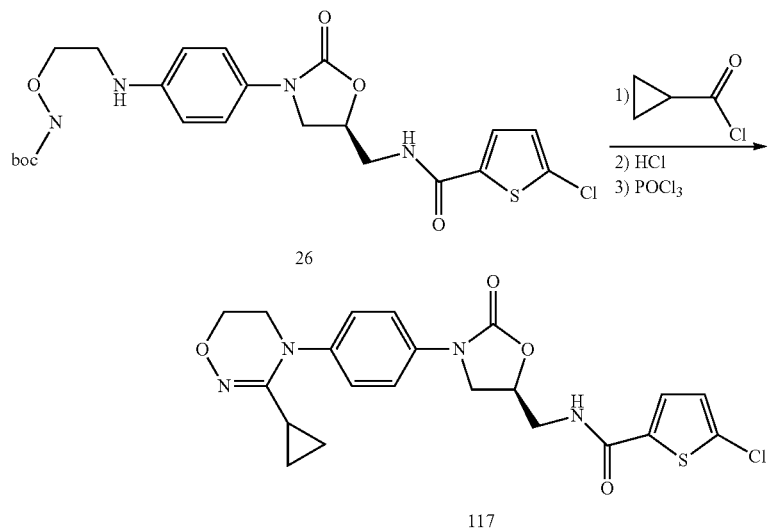

Compound 26 (0.20 mg, 0.39 mmol) obtained in Manufacturing Example 5, cyclopropanecarbonylchloride (50 mg, 0.47 mmol), pyridine (61 mg, 0.78 mmol) and 4-dimethylaminopyridine (5 mg) were added to methylenechloride (5 mL), followed by stirring for 2 hours. Upon completion of the reaction, methylenechloride (50 mL) was added thereto, followed by washing with distilled water (10 mL) twice. After concentration under reduced pressure, column chromatography was performed to give amide compound as a white solid (150 mg, 0.29 mmol, 74%).

$^1$H NMR (400 MHz, DMSO-d$_6$) δ 9.90 (s, 1H), 8.98 (t, J=6.0 Hz, 1H), 7.69 (d, J=4.0 Hz, 1H), 7.62 (d, J=8.8 Hz, 2H), 7.42 (d, J=8.8 Hz, 2H), 7.19 (d, J=4.0 Hz, 1H), 4.84 (m, 1H), 4.21 (t, J=8.8 Hz), 3.87 (dd, J=9.2, 6.4 Hz, 1H), 3.78-3.74 (m, 4H), 3.61 (t, J=5.6 Hz, 2H), 1.22 (m, 1H), 0.78 (m, 2H), 0.59 (m, 2H)

The compound obtained above (0.15 g, 0.29 mmol) was added to 4N HCl (in dioxane) (2 mL), followed by stirring at room temperature for one hour. The reactant was concentrated under reduced pressure. Toluene (5 mL) and phosphorousoxychloride (45 mg, 0.29 mmol) were added thereto, followed by reflux with stirring for 12 hours. Column chromatography was performed to give the title compound 117 as a white solid (11 mg, 0.03 mmol, 10%).

$^1$H NMR (400 MHz, chloroform-d$_1$) δ 7.54 (d, J=8.8 Hz, 2H), 7.31 (d, J=4.4 Hz, 1H), 7.25 (d, J=8.8 Hz, 2H), 6.90 (d, J=4.4 Hz, 1H), 6.55 (t, J=4.8 Hz, 1H), 4.88 (m, 1H), 4.10 (t, J=4.8 Hz, 2H), 3.89 (m, 2H), 3.79 (m, 1H), 3.67 (t, J=4.8 Hz, 2H), 1.06 (m, 1H), 0.93 (m, 2H), 0.58 (m, 2H); LCMS: 461 (M+H$^+$) to C$_{21}$H$_{21}$ClN$_4$O$_4$S

Example 19

Preparation of Compound 118

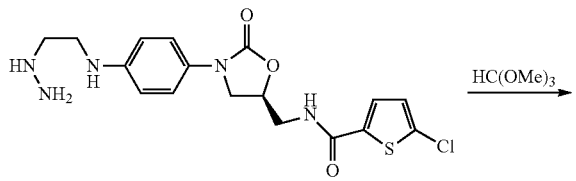

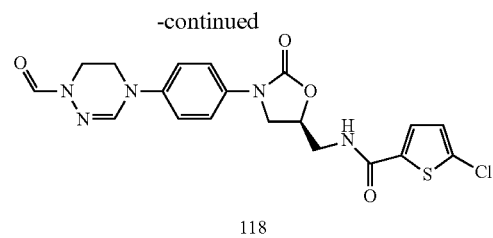

Compound 118 was prepared as a white solid by the similar manner as described in Example 10 by using compound 33 synthesized by the method of reaction formula 5.

$^1$H NMR (400 MHz, chloroform-d$_1$) δ 8.55 (s, 1H), 7.52 (d, J=8.8 Hz, 2H), 7.33 (d, J=4.4 Hz, 1H), 7.10 (s, 1H), 7.05 (d, J=8.8 Hz, 2H), 6.89 (d, J=4.4 Hz, 1H), 6.76 (t, J=4.8 Hz, 1H), 4.88 (m, 1H), 4.11 (t, J=8.8 Hz, 1H), 4.00 (t, J=4.8 Hz, 2H), 3.91-3.77 (m, 3H), 3.74 (t, J=4.8 Hz, 2H); LCMS: 448 (M+H$^+$) to C$_{19}$H$_{18}$ClN$_5$O$_4$S

Example 20

Preparation of Cpound 119

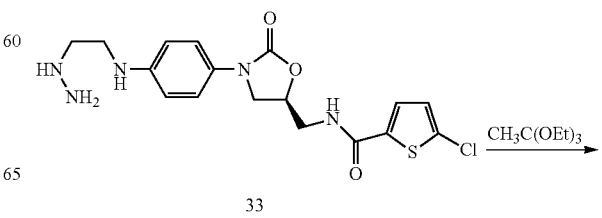

-continued

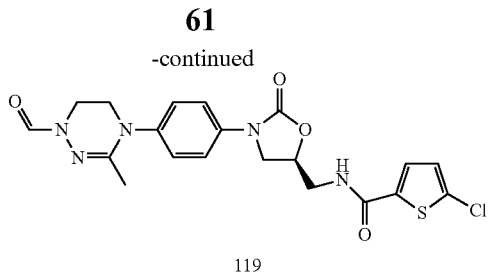

119

Compound 119 was prepared as a white solid by the similar manner as described in Example 14 by using compound 33 synthesized by the method of reaction formula 5.

$^1$H NMR (400 MHz, DMSO-$d_6$) δ 8.94 (br t, 1H), 8.35 (s, 1H), 7.64 (d, J=4.4 Hz, 1H), 7.52 (d, J=8.8 Hz, 2H), 7.26 (d, J=8.8 Hz, 2H), 7.14 (d, J=4.4 Hz, 1H), 4.80 (m, 1H), 4.15 (t, J=8.4 Hz, 1H), 3.81-3.75 (m, 3H), 3.58-3.51 (m, 4H), 1.75 (s, 3H); LCMS: 462 (M+H$^+$) to $C_{20}H_{20}ClN_5O_4S$

Example 21

Preparation of Compound 120

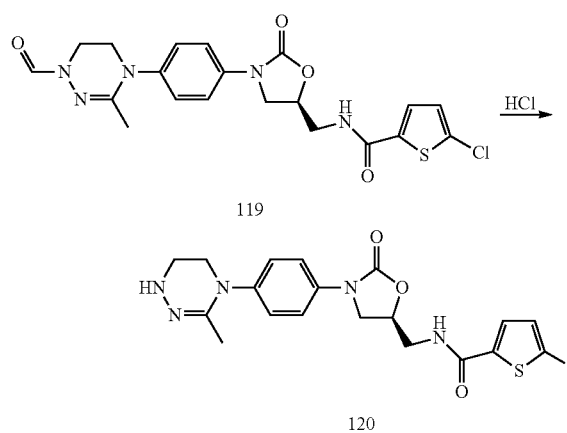

Compound 119 synthesized in Example 20 was dissolved in methanol, followed by deformylation with HCl to give the title compound 120 as a white solid.

$^1$H NMR (400 MHz, DMSO-$d_6$) δ 8.98 (br t, 1H), 7.69 (d, J=4.4 Hz, 1H), 7.52 (d, J=8.8 Hz, 2H), 7.23-7.19 (m, 3H), 4.83 (m, 1H), 4.18 (t, J=8.4 Hz, 1H), 3.84 (m, 1H), 3.61-3.55 (m, 4H), 3.06 (t, J=4.8 Hz, 2H), 1.64 (s, 3H); LCMS: 434 (M+H$^+$) to $C_{19}H_{20}ClN_5O_3S$

Example 22

Preparation of Compound 121

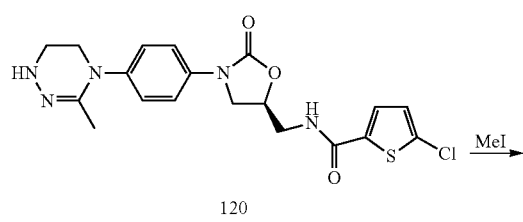

Compound 120 synthesized in Example 21 was reacted with iodomethane to give the title compound 121 as a white solid.

$^1$H NMR (400 MHz, DMSO-$d_6$) δ 8.98 (br t, 1H), 7.69 (d, J=4.4 Hz, 1H), 7.55 (d, J=8.8 Hz, 2H), 7.28 (d, J=8.8 Hz, 2H), 7.19 (d, J=4.4 Hz, 1H), 4.84 (m, 1H), 4.18 (t, J=8.4 Hz, 1H), 3.84 (m, 1H), 3.65-2.92 (m, 6H), 2.60 (s, 3H), 1.67 (s, 3H); LCMS: 448 (M+H$^+$) to $C_{20}H_{22}ClN_5O_3S$

Experimental Example 1

Inhibitory Activity of Factor Xa (FXa) Inhibitor

1) Reagent and Material

S-2765 (N-Z-D-Arg-Gly-Arg-pNA.2HCl), the chromogenic substrate necessary for measuring factor Xa activity, was purchased from Chromogenix. Human FXa was purchased from Enzyme Research Laboratories. 96-well microplate was purchased from Corning Life Sciences.

2) Inhibitory Activity of FXa Inhibitor

Inhibitory activity of the oxazolidinone derivatives with cyclic amidoxime or cyclic amidrazone group represented by formula I of the present invention against FXa was measured as follow.

The activity of the compounds against purified human FXa was measured using chromogenic substrate S-2765 (Z-D-Arg-Gly-Arg-pNA.2HCl) in 96-well microplates at 37° C. Enzymatic activity was assayed in 100 mM Tris-HCl buffer (pH 7.8) containing human FXa (2.6 nM), NaCl (150 mM), PEG 8000 (0.1%), test compound dilutions (1% DMSO), and S-2765 (300 uM). The reaction was initiated by the addition of the substrate, and the absorbance was monitored continuously at 405 nm for 5 min using SpectraMax 190 (Molecular Devices, USA). The inhibitory constant ($K_i$) against human FXa was calculated according to the Cheng-Prusoff equation (Ki=IC$_{50}$/1+[S]/K$_m$), where [S] is the substrate concentration, and K$_m$ is the MichalisMenten constant. K$_m$ was determined from a Lineweaver-Burk plot. The IC$_{50}$ was the amount of inhibitor required to decrease the initial velocity of the control by 50%. IC$_{50}$ values were calculated using GraFit software version 5.0.12 (Erithacus Software Ltd., UK).

Km value used for the calculation is 125 μM, which is obtained by changing the substrate concentration at a constant enzyme concentration.

Experimental Example 2

Effect on Blood Coagulation

Effect of the oxazolidinone derivatives with cyclic amidoxime or cyclic amidrazone group represented by formula I of the present invention on blood coagulation was investigated by measuring prothrombin time (PT).

1) Measurement of PT a) Method using coagulometer: Prothrombin time (PT) was measured with a Thrombotimer 4-channel coagulometer (Behnk Elektronik, Germany). Citrated human and rat plasma were used in the assays. For the PT measurement, 100 uL of freshly thawed plasma was mixed with 3 uL of serial dilution of test compound or DMSO. After 5 min incubation at 37° C., 200 uL of STA-Neoplastine (Diagnostica Stago, France) was added to start clot formation. Anticoagulant activity of the compounds was defined as the concentration required to double the plasma clotting times [2×PT (uM)]. Human plasma was obtained from Daejeon Red Cross Blood Center. Rat blood was withdrawn from the carotid artery or superior vena cava under anesthesia. Blood was collected into plastic tubes containing ¹/₁₀ volume of 3.8% sodium citrate. Plasma was obtained by immediate centrifugation at 2500 g for 10 min at 4° C., and stored at −70° C.

b) Method using spectramax: The compound solution of serial dilution (5 uL) according to the present invention was mixed with citrated plasma (45 uL) followed by addition of STA-Neoplastine (Diagnostica Stago, France) after 5 min at 37° C. Absorbance at 340 nm was continuously monitored and the PT was determined as time (in seconds) when the absorbance at 340 nm reached 0.1. Anticoagulant activity of the compounds was defined as the concentration required to double the plasma clotting times [2×PT (uM)]. Anticoagulant activity of the compounds was defined as the concentration required to double the plasma clotting times [2×PT (uM)]. Human plasma was obtained from Daejeon Red Cross Blood Center. Rat blood was withdrawn from the carotid artery or superior vena cava under anesthesia. Blood was collected into plastic tubes containing ¹/₁₀ volume of 3.8% sodium citrate. Plasma was obtained by immediate centrifugation at 2500 g for 10 min at 4° C., and stored at −70° C.

2) Measurement of Antithrombotic Effect Using Arterio-venous Shunt (AV-Shunt) Model in Rats Antithrombotic effect of the oxazolidinone derivatives with cyclic amidoxime or cyclic amidrazone group represented by formula I of the present invention was evaluated using arteriovenous (AV) shunt in rats. Fasted, male Sprague-Dawley rats, weighed 200-240 g and aged approximately 7 weeks, were anesthetized by intraperitoneal injection of urethane (1.25 g/kg) or chloral hydrate. An arteriovenous (AV) shunt in anesthetized rats was performed as described previously, with minor modification [Journal of Thrombosis and Haemostasis (2004) 3, 514]. The left common carotid artery and the right jugular vein were cannulated with two 200-mm-long, saline filled tubes (PE-50, Becton Dickinson, USA). The polyethylene tubes were connected through 8-mm-long silicone tubing (L/S® 13, MasterFlex, USA) with a 50-mm-long silicone tube (L/S® 16, MasterFlex, USA) containing a 75-mm-long-cotton thread. The compound or vehicle was given orally 60 min before shunt was opened for 15 min. The cotton thread was then withdrawn and weighed. $ED_{50}$ values were calculated by linear regression analysis using Excel 2003 (Microsoft®).

3) Measurement of Bleeding Time (BT) Using Rat Tail Bleeding Model

Fasted, male Sprague-Dawley rats, weighed 200-240 g and aged approximately 7 weeks, were anesthetized by intraperitoneal injection of pentobarbital-Na (60 mg/kg). The FXa inhibitors or vehicle was given orally 60 min before the tails of anesthetized rats were transected 2 mm from the tip and vertically immersed in saline at 37° C. The time until continuous blood flow ceased for >30 s was measured, with a maximum observation time of 30 min (longer bleeding time were assigned a value of 30 min).

Inhibition constant against human FXa, anticoagulant effect (expressed as 2×PT) and antithrombotic effect in rat AV-shunt (expressed as % inhibition of thrombus formation) measured by above experimentals are shown in Table 1. Effect of compounds on rat tail-transection bleeding time is summarized in Table 2. Rivaroxaban represented by formula A was used as the comparison drug.

[Formula A]

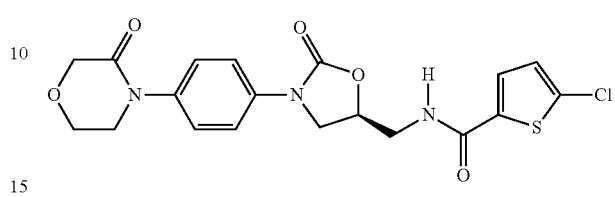

TABLE 1

Inhibition constant against human FXa, anticoagulant effect (expressed as 2xPT) and antithrombotic effect (expressed as % inhibition of thrombus formation) in rat AV-shunt of the compounds of formula I

| Compounds | Ki (nM) | 2xPT (uM) Coagulometer | 2xPT (uM) Spectramax | Inhibition of thrombus formation (%) |
|---|---|---|---|---|
| Rivaroxaban | 0.76 | 0.19 ± 0.03 | 0.09 | 75, 75* |
| 100 | 7.11 | 0.69 ± 0.07 | 0.25 | 65, 58* |
| 101 | 109.75 | — | 1.39 | 45 |
| 102 | 8.91 | 1.76 | 0.77 | 61 |
| 103 | 53.32 | — | 1.10 | 24 |
| 104 | 10.01 | — | 0.05 | 21 |
| 105 | 3.62 | 0.16 | 0.04 | 80 |
| 106 | >30 | — | 0.33 | — |
| 107 | 15.96 | — | 0.16 | 37 |
| 108 | 15.84 | 1.00 | 0.35 | 52 |
| 109 | 4.37 | 0.44 | 0.21 | 78, 73* |
| 110 | 2.07 | 0.31 | — | 45* |
| 111 | 18.9 | 0.40 | — | 17* |
| 112 | 120.13 | 4.26 | — | 44* |
| 113 | 29.34 | 0.62 | — | 12* |
| 114 | 2.86 | 0.50 | — | 5* |
| 115 | 83.97 | — | 1.49 | 29 |
| 116 | 23.22 | 3.51 | 0.71 | 74 |
| 117 | 101 | — | 2.2 | — |
| 118 | 132.05 | 9.38 | 4.88 | 74 |
| 119 | 64.43 | 4.77 | 2.53 | 72 |
| 120 | 645.19 | — | 3.75 | 43 |
| 121 | 95.60 | 2.90 | 0.54 | 51 |

*Urethane was used as an anestheic. For asterisked compounds, chloral hydrate was used instead.

As shown in Table 1, the oxazolidinone derivatives with cyclic amidoxime or cyclic amidrazone group represented by formula I of the present invention had similar Ki value and PT value to those of the comparison drug Rivaroxaban. In rat AV-shunt model, antithrombotic effect was comparable to that of Rivaroxaban, even though a little variation in antithrombotic effect was found depending on anesthetics used. The most serious side effect of Rivaroxaban is bleeding. Tail bleeding time was evaluated at the multiple doses to investigate bleeding effect of the representative compounds presented by formula I. Effect of Compound 100, 109 and the comparison drug Rivaroxaban on rat tail transection bleeding time is summarized in Table 2.

TABLE 2

Effect of compound 100 and 109 on rat tail bleeding time (n = 13)

| Compounds | Prolongation of bleeding time (X-fold) Dose (mg/kg, po) | | | | |
|---|---|---|---|---|---|
| | 1.25 | 2.5 | 5 | 10 | 20 |
| Rivaroxaban | 3.5 | 5.0 | 7.0 | | |
| 100 | | | 0.9 | | |
| 100 (HCl salt) | | | 1.2 | 0.9 | |
| 100 (MSA salt) | | | 1.1 | 1.8 | 5.1 |
| 109 | | 2.5 | 4.0 | 4.1 | |
| 109 (MSA salt) | | 2.1 | 3.8 | 5.7 | |

In rat tail bleeding model, the compound 100 did not prolonged bleeding time even at 10 mg/kg compared to the vehicle control. On the other hand, Rivaroxaban caused prolongation of bleeding time three to four fold even at 1.25 mg/kg. Compounds of formula I were, therefore, confirmed to lower the side effect (bleeding) significantly. Besides, compounds of formula I can be formulated as a salt using an acid such as methanesulfonic acid or HCl so that aqueous solubility can be improved. Aqueous solubility was measured by the following experiment.

Experimental Example 3

Measurement of Aqueous Solubility

Compound 100 and 109, the representative oxazolidinone derivative with cyclic amidoxime group (100) and cyclic amidrazone group (109) of formula I of the present invention, in the form of hydrochloride or methanesulfonate (MSA) were tested for aqueous solubility and the results are shown in Table 3. Rivaroxaban represented by formula A was used as the comparison drug.

TABLE 3

Aqueous solubility of compound 100 and 109 in the form of hydrochloride and methanesulfonate

| Compounds | Aqueous Solubility (mM) |
|---|---|
| Rivaroxaban | <0.05 |
| 100-HCl | 12 |
| 100-MSA | >20 |
| 109-HCl | 6 |
| 109-MSA | >20 |

As shown in Table 3, the oxazolidinone derivative with cyclic amidoxime (100) or cyclic amidrazone (109) group of formula 1 of the present invention has a great advantage of being prepared in the form of salt, and therefore it can have excellent aqueous solubility 200 fold as high as that of Rivaroxaban, the control material. This result indicates that the oxazolidinone derivatives with cyclic amidoxime or cyclic amidrazone group of formula 1 of the present invention has high usability as a composition for oral administration and injection.

As explained hereinbefore, the oxazolidinone derivatives with cyclic amidoxime or cyclic amidrazone group of formula 1 of the present invention shows almost no bleeding, one of the serious side effects of the conventional drug such as Rivaroxaban, but has similar inhibition activity to Rivaroxaban, and has excellent solubility, so that it can have excellent usability as a composition for oral administration and injection.

INDUSTRIAL APPLICABILITY

The novel oxazolidinone derivatives with cyclic amidoxime or cyclic amidrazone group represented by formula 1 of the present invention can be a very safe drug which does not increase bleeding, the serious side effect of Rivaroxaban which is the control material in this invention, and has higher aqueous solubility than Rivaroxaban, so that it can be easily developed as a composition for oral administration or injection.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An oxazolidinone compound with cyclic amidoxime or cyclic amidrazone group, represented by formula 1, an in vivo hydrolysable ester formed on ring A of formula 1, an isomer or a pharmaceutically acceptable salt thereof:

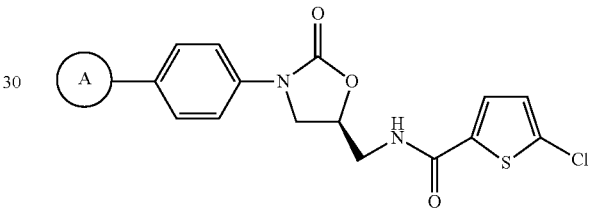

Formula I wherein,
ring A is a residue selected from the group consisting of following structure:

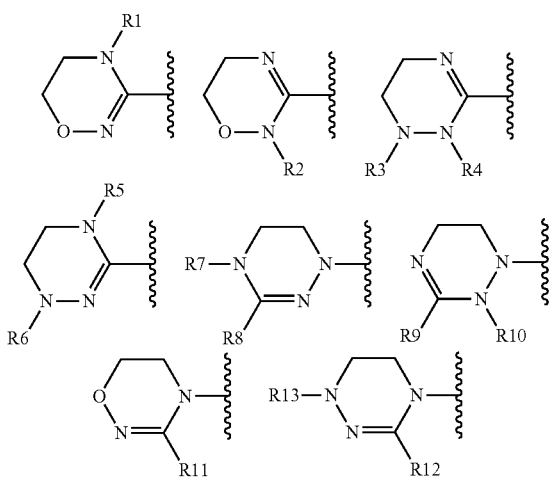

$R_1$ through $R_{12}$, independently of one another, represent hydrogen, a $(C_1\text{-}C_7)$alkyl, $(C_3\text{-}C_7)$cycloalkyl, $(C_6\text{-}C_{12})$aryl or $(C_4\text{-}C_{12})$heteroaryl containing one to four heteroatom(s) selected from the group consisting of O, S and N, or $R_3$ and $R_4$ form a ring by connecting with $(C_3\text{-}C_5)$alkylene, carbon atom of the alkylene can be substituted with an oxo, alkyl, cycloalkyl, aryl or heteroaryl of the $R_1$ through $R_{12}$ may be substituted with any one selected from the group consisting of $(C_1-C_7)$alkyl, halo$(C_1-C_7)$alkyl, $(C_1-C_7)$alkoxy and halogen; and $R_{13}$ is H, $(C_1-C_7)$alkyl, $(C_3-C_7)$cycloalkyl, formyl, $(C_1-C_7)$alkylcarbonyl, $(C_1-C_7)$alkoxycarbonyl or $(C_6-C_{12})$aryl.

2. The oxazolidinone compound, in vivo hydrolysable ester, isomer or pharmaceutically acceptable salt thereof according to claim 1, wherein the oxazolidinone derivative is selected from the following formula II to formula XI:

Formula II

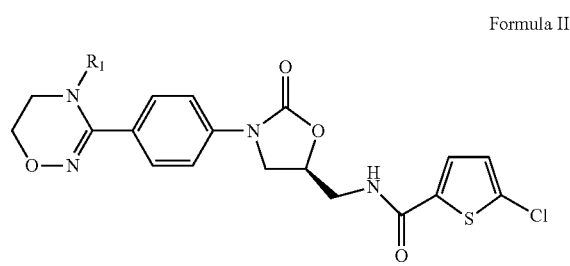

Formula III

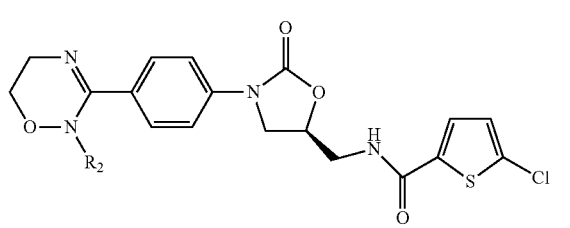

Formula IV

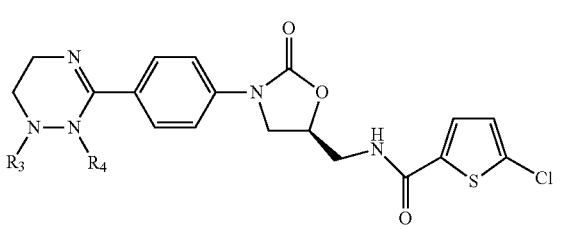

Formula V

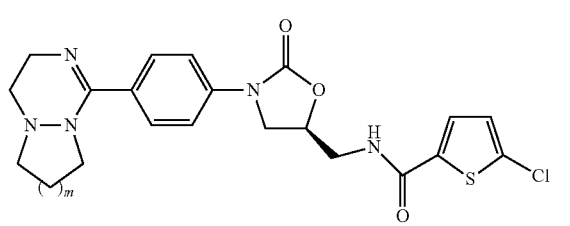

Formula VI

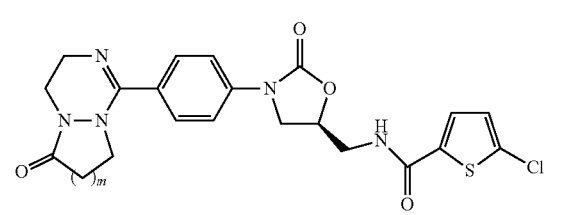

Formula VII

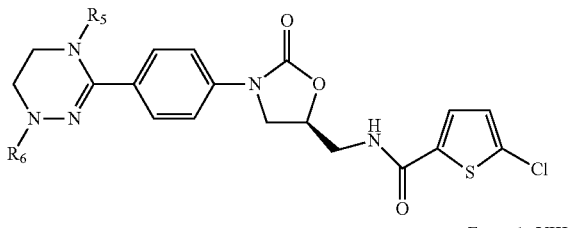

Formula VIII

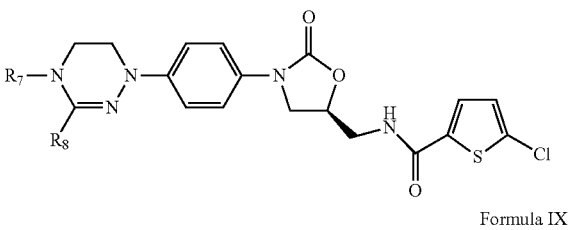

Formula IX

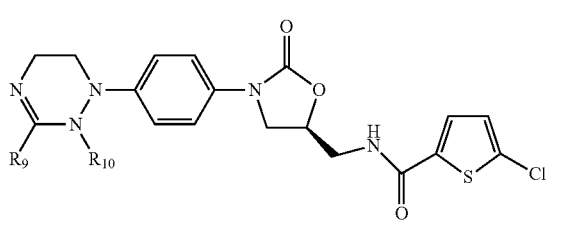

Formula X (image of Formula X)

Formula XI (image of Formula XI)

wherein,
$R_1$ through $R_{12}$, independently of one another, represent hydrogen, a $(C_1-C_7)$alkyl or $(C_3-C_7)$cycloalkyl; $R_{13}$ is H, a $(C_1-C_7)$alkyl, $(C_3-C_7)$cycloalkyl, formyl or $(C_1-C_7)$alkylcarbonyl; and m is an integer from 1 to 3.

3. The oxazolidinone compound, in vivo hydrolysable ester, isomer or pharmaceutically acceptable salt thereof according to claim 2, wherein the $R_1$ through $R_{12}$, independently of one another, represent hydrogen, methyl, ethyl, n-propyl, i-propyl, n-butyl, i-butyl, t-butyl, cyclopropyl, cyclobutyl, cyclopentyl or cyclohexyl; the $R_{13}$ is H, methyl, ethyl, n-propyl, i-propyl, n-butyl, i-butyl, t-butyl, cyclopropyl, cyclobutyl, cyclopentyl, cyclohexyl, formyl or acetyl; and the m is an integer of 1.

4. The oxazolidinone compound, in vivo hydrolysable ester, isomer or pharmaceutically acceptable salt thereof according to claim 3, wherein said the oxazolidinone compound is selected from the following compounds:

69
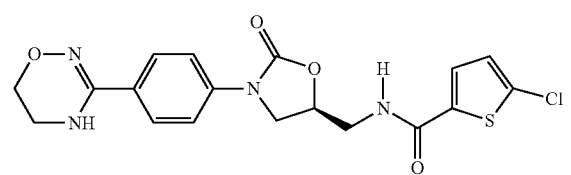
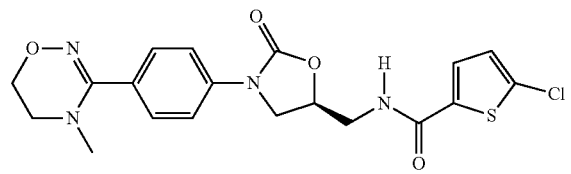
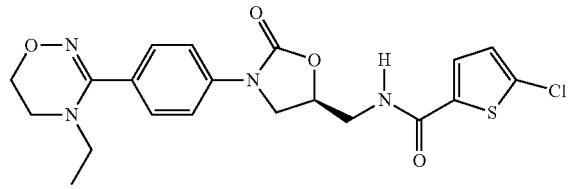
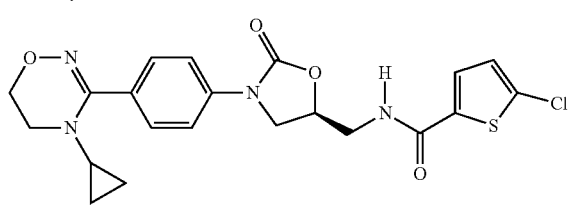
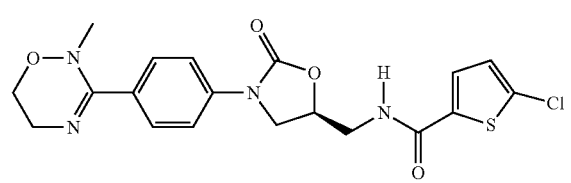
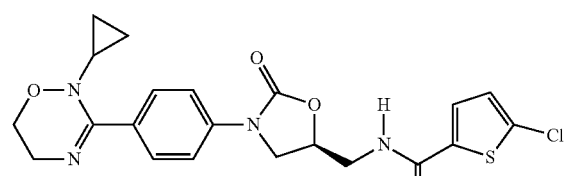
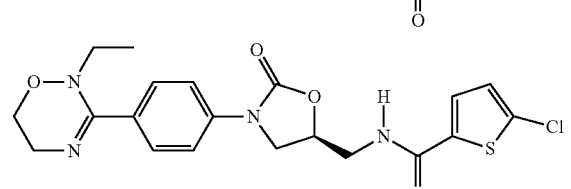
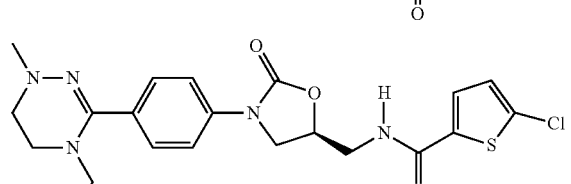
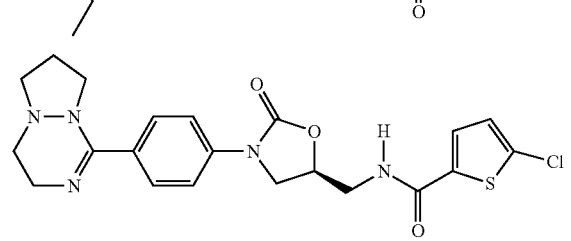
70
-continued
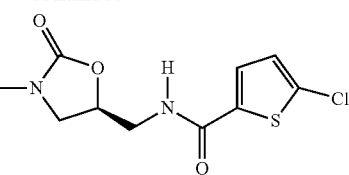
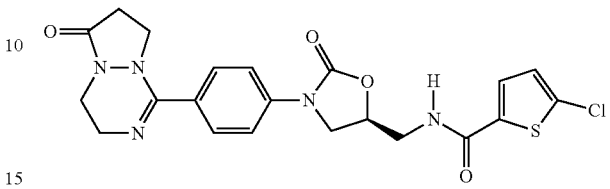
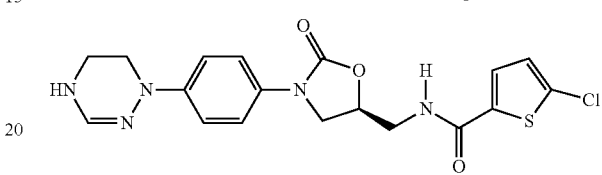
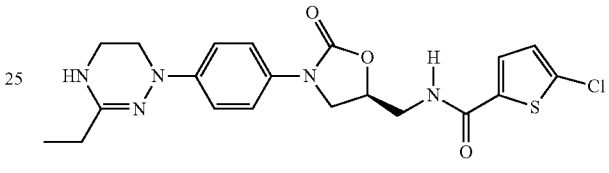
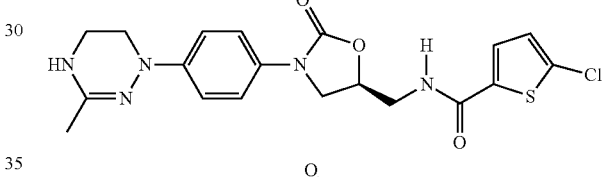
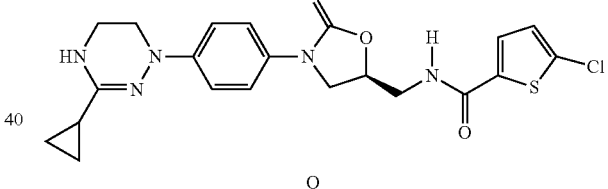
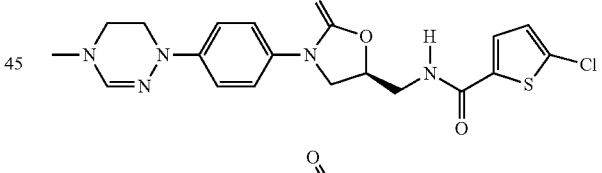
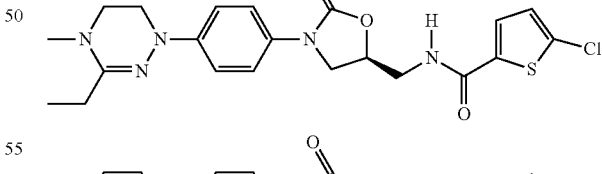
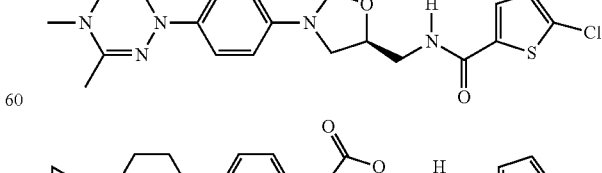
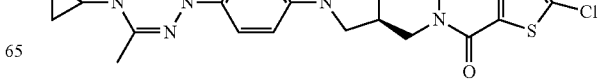

71
-continued

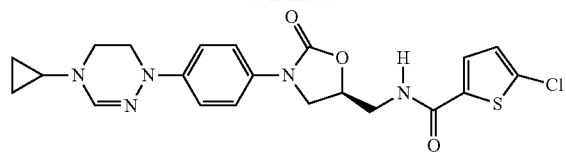
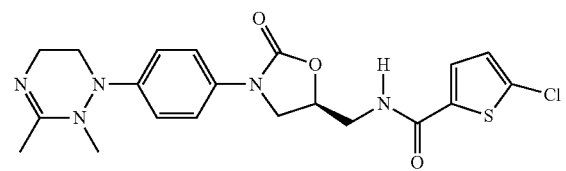
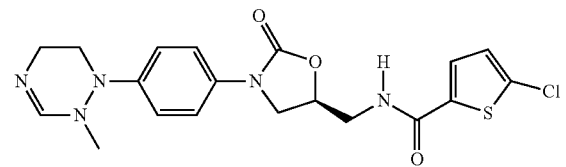
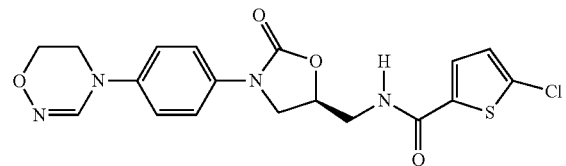
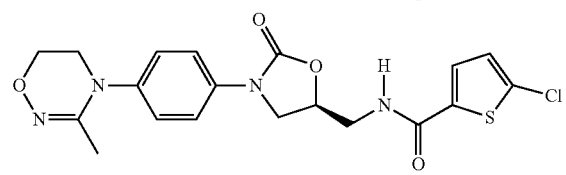
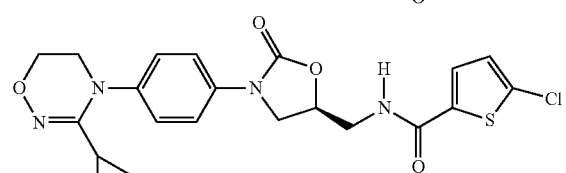
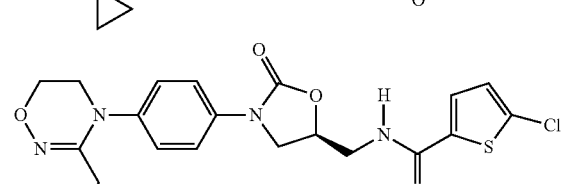

72
-continued

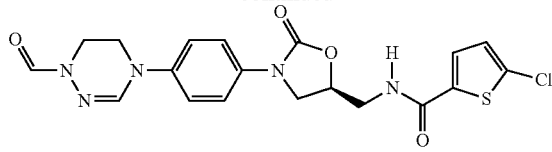
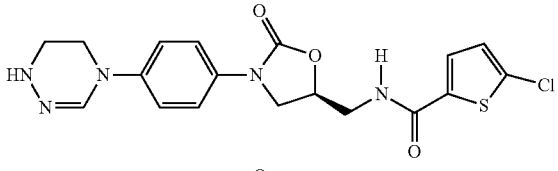
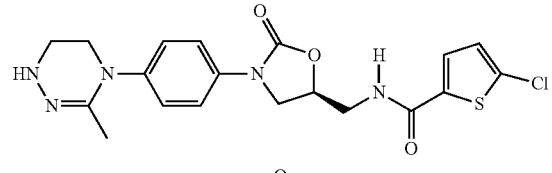
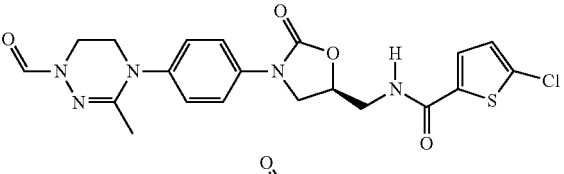
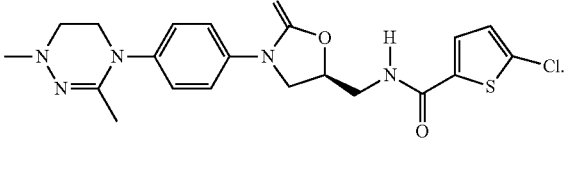
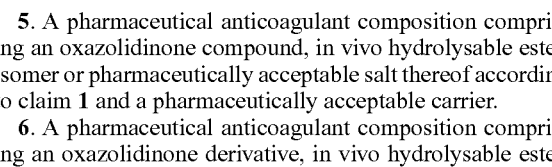

5. A pharmaceutical anticoagulant composition comprising an oxazolidinone compound, in vivo hydrolysable ester, isomer or pharmaceutically acceptable salt thereof according to claim 1 and a pharmaceutically acceptable carrier.

6. A pharmaceutical anticoagulant composition comprising an oxazolidinone derivative, in vivo hydrolysable ester, isomer or pharmaceutically acceptable salt thereof according to claim 1, in combination with a thrombolytic drug, and a pharmaceutically acceptable carrier.

7. An anticoagulant composition comprising an oxazolidinone derivative, in vivo hydrolysable ester, isomer or pharmaceutically acceptable salt thereof according to claim 1 in an effective amount, for preserving blood, plasma or blood products in vitro.

* * * * *